(12) United States Patent
Berg et al.

(10) Patent No.: US 6,680,301 B2
(45) Date of Patent: *Jan. 20, 2004

(54) TRANSFER OF MOLECULES INTO THE CYTOSOL OF CELLS

(75) Inventors: Kristian Berg, Heggedal (NO); Kirsten Sandvik, Oslo (NO); Johan Moan, Oslo (NO); Anders Høgset, Oslo (NO)

(73) Assignee: Photocure AS, Oslo (NO)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/144,750

(22) Filed: Sep. 1, 1998

(65) Prior Publication Data

US 2002/0155099 A1 Oct. 24, 2002

Related U.S. Application Data

(63) Continuation-in-part of application No. 08/793,794, filed as application No. PCT/NO95/00149 on Sep. 4, 1995, now Pat. No. 5,876,989.

(30) Foreign Application Priority Data

Sep. 8, 1994 (NO) ............................................... 943327

(51) Int. Cl.⁷ ............................................... A61K 48/00
(52) U.S. Cl. ....................... 514/44; 435/69.1; 435/91.3; 435/320.1; 435/325; 435/455
(58) Field of Search .................... 435/6, 320.1, 325, 435/69.1, 91.3, 455; 514/2, 514; 424/37.21; 536/23.1, 24.5

(56) References Cited

U.S. PATENT DOCUMENTS

| | | |
|---|---|---|
| 4,649,151 A | 3/1987 | Dougherty et al. .......... 514/410 |
| 5,059,619 A | 10/1991 | Haeger et al. ............... 514/410 |
| 5,066,274 A | 11/1991 | Bommer et al. .............. 604/20 |
| 5,095,030 A | 3/1992 | Levy et al. .................. 514/410 |
| 5,095,097 A | 3/1992 | Hermentin et al. .......... 530/388 |
| 5,179,120 A | 1/1993 | Vogel et al. ................. 514/410 |
| 5,256,532 A | 10/1993 | Melnicoff et al. ............. 439/5 |
| 5,264,344 A | 11/1993 | Sneath ....................... 439/7.32 |
| 5,328,470 A * | 7/1994 | Nabel et al. .................. 514/44 |
| 5,374,531 A | 12/1994 | Jensen ....................... 435/7.24 |
| 5,424,213 A | 6/1995 | Mougin ....................... 436/63 |
| 5,491,068 A | 2/1996 | Benjamin et al. ........... 435/7.32 |
| 5,514,340 A | 5/1996 | Lansdorp et al. ............ 422/101 |
| 5,536,644 A | 7/1996 | Ullman et al. ............... 435/7.25 |
| 5,567,687 A * | 10/1996 | Magda et al. | |
| 5,624,815 A | 4/1997 | Grant et al. .................. 435/30 |
| 5,703,054 A * | 12/1997 | Bennett et al. ............... 514/44 |
| 5,789,248 A * | 8/1998 | Fodstad et al. | |
| 5,861,310 A * | 1/1999 | Freeman et al. ............. 435/325 |
| 5,876,989 A * | 3/1999 | Berg et al. ................... 435/455 |
| 5,877,308 A * | 3/1999 | Fodstad et al. | |
| 5,985,620 A * | 11/1999 | Sioud ....................... 435/91.31 |
| 6,015,897 A * | 1/2000 | Theodore et al. | |

FOREIGN PATENT DOCUMENTS

| | | |
|---|---|---|
| EP | 0 098 534 | 1/1984 |
| EP | 0 131 934 | 1/1985 |
| EP | 0 339 769 | 11/1989 |
| GB | 2 209 468 * | 5/1989 |
| NO | 891491 | 4/1989 |
| NO | 924151 | 10/1992 |
| NO | 173319 | 12/1993 |
| NO | 934837 | 12/1993 |
| NO | 176645 | 5/1995 |
| NO | 176947 | 6/1995 |
| NO | 176786 | 7/1995 |
| NO | 179410 | 10/1996 |
| NO | 180742 | 3/1997 |
| WO | WO 89/01630 | 2/1989 |
| WO | WO 90/00393 | 1/1990 |
| WO | WO 91/01368 | 2/1991 |
| WO | WO 91/09938 | 7/1991 |
| WO | WO 92/04961 | 4/1992 |
| WO | WO 93/14142 * | 7/1993 |
| WO | WO 93/22443 * | 11/1993 |
| WO | WO 94/07138 | 3/1994 |
| WO | WO 94/07139 | 3/1994 |
| WO | WO 95/24648 | 9/1995 |
| WO | WO 96/07432 | 3/1996 |

OTHER PUBLICATIONS

Marshall, Science, vol. 269, pp. 1050–1055, 1995.*
Verma, Nature, vol. 389, pp. 239–242, 1997.*
PNAS, vol. 90, pp. 7879–83, 1993.*
Hallenbeck, P.L. and Stevenson, S.C., Adv. Exp. Med. Biol., *Targetable Gene Delivery Vectors*, 2000, 465, 37–46.
Bueler, H., Biolog. Chem., *Ademo–Associated Viral Vectors for Gene Transfer and Gene Therapy*, 1999, 380, 613–622.
Rini, B.I. et al., Clin. Cancer Res., *Phase I Study of Direct Intralesional Gene Transfer of HLA–B7 in to Metastatic Renal Carcinoma Lesions*, 1999, 5, 2766–2772.
Blackwell, J.L. et al., Arch. Otolaryngol. Head Neck Surg., *Retargeting to EGFR Enhances Adenovirus Infection Efficiency of Squamous Cell Carcinoma*, 1999, 125, 856–863.
Bouri, K. et al. Hum. Gene Ther., *Polylysine Modification of Adenoviral Fiber Protein Enhances Muscle Cell Transduction*, 1999, 10, 1633–1640.

(List continued on next page.)

Primary Examiner—Dave T. Nguyen
(74) Attorney, Agent, or Firm—Merchant & Gould, P.C.

(57) ABSTRACT

The present invention relates to a method for introducing molecules in cells by disrupting endosomal and lysosomal membranes using photodynamic treatment, without killing the majority of the cells by the photodynamic treatment. More particularly, this invention includes a method for transferring DNA and/or RNA, such as genes, to cells by photochemically inducing the disruption of endosomes and lysosomes.

14 Claims, 28 Drawing Sheets

OTHER PUBLICATIONS

G. Romano, In Vivo, *Recent Advances, Prospects and Problems in Designing New Strategies for Oligonucleotide and Gene Delivery in Therapy*, 1998, 12, 59–57.

Dachs, G.U. et al., Oncol. Res., *Targeting Gene Therapy to Cancer: A Review*, 1997, 9, 313–325.

Anderson, W.F., Nature, *Human Gene Therapy*, 1998, 392, 25–30.

Luo, D. and Saltzman, W.M., Nat. Biotechnol., *Synthetic DNA delivery systems*, 2000, 18, 33–37.

Cotton, M. et al., Proc. Natl. Acad. Sci, *Transferrin–polycation–mediated introduction of DNA into human leukemic cells: Stimulation by agents that affect the survival of transfected DNA or modulate transferrin receptor levels*, 1990, 87, 4033–4037.

Leamon and Low, Proc. Natl. Acad. Sci., *Delivery of macromolecules into living cells: A method that exploits folate receptor endocytosis*, 1991, 88, 5572–5576.

Bramson, J.L. et al., Hum. Gene Ther., *Direct Intratumoral Injection of an Adenovirus Expressing Interleukin1–2 Induces Regression and Long–Lasting Immunity That is Associated with Highly Localized Expression of Interleukin–12*, 1996, 7, 1995–2002.

Yovandich et al., Hum. Gene Ther., *Gene Transfer to Synovial Cells by Intra–Articular Administration of Plasmid DNA*, 1995, 6, 603–610.

Sikes et al., Hum. Gene Ther., *In Vivo Gene Transfer into Rabbit Thyroid Follicular Cells by Direct DNA Injection*, 1994, 5, 837–844.

Lee, R.J., and Huang, L., J. Biol. Chem, *Folate–targeted, Anionic Liposome–entrapped Polylysine–condensed DNA for Tumor Cell–specific Gene Transfer*, 1996, 271, 8481–8487.

Stone, D. et al., J. Endocrinol., *Viral vectors for gene delivery and gene therapy within the endocrine system*, 2000, 164, 103–118.

Gabaglia, C.R. et al., J. Immunol., *A Single Intramuscular Injection with an Adenovirus–Expressing IL–12 Protects BALB/c Mice Against Leishmania major Infection, While Treatment with an IL–4–Expressing Vector Increases Diseases Disease Susceptibility in B10.D2 Mice*, 1999, 162, 753–760.

Tursz, T. et al., J. Natl. Cancer Inst., *Phase I Study of a Recombinant Adenovirus–Mediated Gene Transfer in Lung Cancer Patients*, 1996, 88, 1857–1869.

Swisher, S.G. et al., J. Natl. Cancer Inst., *Adenovirus–Mediated p53 Gene Transfer in Advanced Non–Small–Cell Lung Cancer*, 1999, 91, 763–767.

Gleich, L.L., Larygoscope, *Gene Therapy for Head and Neck Cancer*, 2000, 110, 708–726.

Verma, I.M. and Somia, N., Nature, *Gene Therapy–promises, problems, and prospects*, 1997, 389, 239–242.

Wickham, T.J. et al., J. Virol., *Targeted Adenoviurs–Mediated Gene Delivery to T Cells via CD3*, 1997, 71, 7663–7669.

Shalev, M. et al., J. Urol., *Suicide Gene Therapy Toxicity After Multiple and Repeat Injections in Patients with Localized Prostate Cancer*, 2000, 163, 1747–1750.

Addison, C.L. et al., Proc. Natl. Acad. Sct. USA, *Intratumoral injection of an adenovirus expressing interleukin 2 induces regression and immunity in a murine breast cancer model*, 1995, 92, 8522–8526.

Herman, J.R. et al., Hum. Gene Ther., *In Situ Gene Therapy for Adenocarcinoma of the Prostate: A Phase I Clinical Trial*, 1999, 10, 1039–1049.

J.J. Zhao, G. Lemke, MCN, *Methods Rules for Ribozymes*, 1998, 92–97.

Sandmair, A.M. et al., Adv. Exp. Med. Biol., *Adenoviruses as gene delivery vectors*, 2000, 465, 423–429.

Gauldle, J., Curr. Pharmaceut. Design, *Gene Vectors for Cytokine Expression in Vivo*, 2000, 6, 613–632.

Garnett, M.C., Crlt. Rev. Ther. Drug Carrier Sys., *Critical Reviews in Therapeutic Drug Carrier Systems*, 1999, 16, 147–207.

Pasqualini, R et al., Nat. Biotechnol., *Integrins as receptors for tumor targeting by circulating ligands*, 1997, 15, 542–546.

Roth, J.A. et al., Semin Oncol., *Gene Therapy for Non–Small Cell Lung Cancer: A Preliminary Report of a Phase I Trial of Adenoviral p53 Gene Replacement*, 1998., 23, 33–37.

Curiel, D.T., Ann. New York Acad. Sci., *Strategies to Adapt Vectors for Targeted Delivery*, 1999, 886, 158–71.

Kircheis, R. et al., J. Gene Med., *Polycation–Based DNA Complexes for Tumor Targeted Gene Delivery in vivo*, 1999, 1, 111–120.

J. DeShane, Gynecol. Oncol., *Transductional Efficacy and Safety of an Intraperitoneally Delivered Adenovirus Encoding an Anti–erbB–2 Intracellular Single–Chain Antibody for Ovarian Cancer Gene Therapy*, 1997, 64, 378–385.

Robbins, P.D. and Ghivizzani, S.C., Pharmacol. Therapeut, *Viral Vectors for Gene Therapy*, 1998, 80, 35–47.

De Smedt, S.C. et al., Pharm. Res., *Cationic Polymer Based Gene Delivery Systems*, 2000, 17, 113–126.

Prasmickaite, L. et al., Nucl. Acids Res, *Intracellular metabolism of a 2'–O–methyl–stabilized ribozyme after uptake by DOTAP transfection or as free ribozyme. A study by capillary electrophoresis*, 1998, 26, 4241–4248.

Oseroff, A. R. et al., Proc. Natl. Acad. Sci. USA, *Antibody–targeted photolysis: Selective photodestruction of human T–cell leukemia cells using monoclonal antibody–chlorin cojugates*, 1986, 83, 8744–8748.

Zenke et al., Proc. Natl. Acad. Sci. *Receptor–mediated endocytosis of transferrin–polycation conjugates: An efficient way to introduce DNA into hematopoietic cells*, 1990, 87, 3655–3659.

Herman, J.R. et al., Hum. Gene Ther., *An RGD–Oligolysine Peptide: A Prototype Construct for Intergin–Mediated Gene Delivery*, 1998, 9, 1037–1047.

Harbottle et al., Hum. Gene Ther., *An RGD–Oligolysine Peptide: A Prototype Construct for Intergin–Mediated Gene Delivery*, 1998, 9, 1037–1047.

Sterman, D.H. et al., Hum. Gene. Ther., *Adenovirus–mediated Herpes Simplex Virus Thymidine Kinase/Ganciclovir Gene Therapy in Patients with Localized Maligancy: Results of a Phase I Clinical Trial in Malignant Mesothelioma*, 1998, 9, 1083–1092.

Del Governatore, M. et al., Br. J. Cancer, *Targeted photodestruction of human colon cancer cells using charged 17.1A aholrin immunoconjugates*, 2000, 82, 56–64.

Bilbao, G. et al., Gene Therapy of Cancer, *Targeted Adenoviral Vectors for Cancer Gene Therapy*, 1998, 451, 365–374.

W.W. Zhang et al., Cancer Gene Ther., Development and application of adenoviral vectors for gene therapy of cancer, 1999, 6–113–138.

Freeman, S. et al., Canoer Res, *The "Bystander Effect": Tumor Regression When a Fraction of the Tumor Mass is Genetically Modified*, 1993, 53, 5274–5283.

Chonn, A. and Cullis, P.R., Adv. Drug Deliv. Rev., *Recent advances in lipsome technologies and their applications for systemic gene delivery*, 1998, 30, 73–83.

Clayman, Gary L., Clin. Cancer Res., *Adenovirus–mediated Wild–Type p53 Gene Transfer as a Surgical Adjuvant in Advanced Head and Neck Cancers*, 1999, 5, 1715–1722.

Wildner, Oliver, Ann. Med., *In situ of suicide genes for therapy of brain tumors*, 1999, 31, 421–429.

Bennick et al., "A Rapid Method for Selecting Specific Hybridoma Clones using Paramagnetic Dynabeads®", *Scand. J. Immunol.*, 38:212–214 (1993).

Haukanes et al., "Application of Magnetic Beads in Bioassays", *Bio/Technology*, 11:60–63 (Jan. 1993).

Heldrup, J., "A New Technique Using an Aggregating Antibody Against Glycophorin—A for Puring FicollPaque–Separated Leucocytes of Contaminating Erythroid Lineage Cells", *Scand. J. Immunol.*, 31:289–296 (1990).

Kopecek, J. et al., "Targetable photoactivatable polymeric drugs", Journal of Controlled Release v. 16, pp. 137–144 (1991).

Pilling et al., "The Kinetics of interaction between lymphocytes and magnetic polymer particles", *J. of Immunol. Methods*, 122:235–241 (1989).

Rye et al., "Immunobead Filteration", *Am. J. Pathology*, 150(1):99–106 (Jan. 1997).

International Search Report dated Jun. 22, 1995.

International Search Report dated Dec. 21, 1995.

Zdolsek, et al., "Photooxidative damage to lysosomes of cultured macrophages by acridine orange", Dep. Pathol. II, Univ. Linkoeping, Linkoeping, S–581 85, Swed., Photochem. Photobiol. (1990), 51(1), 67–76 –Abstract.

* cited by examiner

SEQUENCE LISTING

```
<160> NUMBER OF SEQ ID NOS:  1

<210> SEQ ID NO 1
<211> LENGTH: 37
<212> TYPE: RNA
<213> ORGANISM: Ribozyme
<220> FEATURE:
<221> NAME/KEY: modified_base
<222> LOCATION: (20)
<223> OTHER INFORMATION: n is a uracil with fluorescein attached

<400> SEQUENCE: 1
uaguucucug augaggccgn uaggccgaaa cuuguuy                              37
```

TRANSFER OF MOLECULES INTO THE CYTOSOL OF CELLS

This application is a continuation-in-part application of application serial No. 08/793,794 filed Mar. 28, 1997, now U.S. Pat. No. 5,876,989.

FIELD OF THE INVENTION

The present invention relates to a method for introducing molecules in cells by disrupting endosomal and lysosomal membranes using photodynamic treatment, without killing the majority of the cells by the photodynamic treatment. More particularly, this invention includes a method for transferring DNA and/or RNA, such as genes, to cells by photochemically inducing the disruption of endosomes and lysosomes.

BACKGROUND OF THE INVENTION

The majority of molecules do not readily penetrate cell membranes. Methods for introducing molecules into the cytosol of living cells are useful tools for manipulating and studying biological processes. Among the most commonly used methods today are microinjection, red blood cell ghost mediated fusion, liposome fusion, osmotic lysis of pinosomes, scrape loading, electroporation, calcium phosphate, and virus mediated transfection. These techniques are useful for investigations of cells in culture, although in many cases impractical, time consuming, inefficient, or they induce significant cell death. They are thus not optimal for use in biological and medical research or therapeutic applications in which the cells should remain functional.

It is well known that porphyrins and many other photosensitizing compounds induce cytotoxic effects on cells and tissues. These effects are based upon the fact that the photosensitizing compound upon light exposure releases singlet $^1O_2$ which decomposes the membranes of the cells and cell structures, and eventually kills the cells if the destruction is extensive. These effects have been utilized to treat several types of neoplastic diseases. The treatment is named photodynamic therapy (PDT) and is based on injection of a photosensitizing and tumorlocalizing dye followed by exposure of the tumor region to light. The cytotoxic effect is mediated mainly through the formation of singlet oxygen. This reactive intermediate has a very short lifetime in cells (<0.04 µs). Thus, the primary cytotoxic effect of PDT is executed during light exposure and very close to the sites of formation of $^1O_2$. $^1O_2$ reacts with and oxidize proteins (histidine, tryptophan, methionine, cysteine, tyrosine), DNA (guanine), unsaturated fatty acids and cholesterol. One of the advantages of PDT is that tissues unexposed to light will not be affected.

There is extensive documentation regarding use of PDT to destroy unwanted cell population, for example neoplastic cells. Several patents relate to photodynamic compounds alone or conjugated with immunoglobulins directed to neoplastic cell receptor determinants making the complex more cell specific. Certain photochemical compounds, such as hematoporphyrin derivates have furthermore an inherent ability to concentrate in malignant cells. These methods and compounds, which are directed to destroy the unwanted cells are described in the Norwegian patent NO 173319, in Norwegian patent applications Nos. 90 0731, 90 2634, 90 1018, 94 1548, 85 1897, 93 4837, 92 4151 and 89 1491.

In PCT/US93/00683 a drug delivery system is described which comprises an anticancer drug and a photoactivatable drug attached to copolymeric carriers. Upon administration this complex enters the cell interior by pinocytosis or phagocytosis and will be located inside the endosomes and lysosomes. In the lysosomes the bond between the antineoplastic compound and the polymer is hydrolyzed, and the former can diffuse passively through the lysosome membrane into cytosol. Thus, this method is limited to small molecular compounds which are able to diffuse across the lysosome membranes. After allowing a time lag for diffusion, a light source of appropriate wavelength is applied to activate the photoactive compound. The combined effects of the anticancer drug and photoactive drug destroy the cell.

Thus, all known use of photoactive compounds is directed to extensively destroy cell structures leading to cell death. A method which releases membrane impermeable molecules into the cytosol after localized rupturing of endosomal/lysosomal membranes is not known.

Desirable molecules for delivery into the cytosol include DNA and/or RNA in the form, for example, of oligonucleotides, oligodeoxynucleotides, ribozymes, antisense molecules, coding sequences, and the like. Once delivered these molecules can be transcribed, expressed, disrupt gene expression, transcription, or translation, or have like effects. For example, gene therapy, i.e. therapeutic transfer of genes to a patient's cells, is a promising method for treating many genetic disorders such as cancer, cystic fibrosis, cardiovascular diseases and many other diseases. Gene therapy includes delivery of a DNA or RNA into the cytosol of a particular cell followed, typically, by an effect in the cytosol or nucleus. However, the DNA or RNA must be delivered to a particular cell or organ and the expression of a therapeutic gene outside the diseased area often can give severe side effects. Many currently existing gene therapy methods lack this desired specificity. Delivery into a cell cytosol or nucleus of DNA and/or RNA for purposes other than gene therapy, for example of antisense or ribozymes, can also be problematic.

SUMMARY OF THE INVENTION

The present invention provides a method to transport molecules, including DNA and/or RNA, into the cytosol of living cells, in culture or in tissues. The method includes exposing the cells to a photoactive compound, or photosensitizer, and the molecule(s) which is (are) to be transported into the cytosol, exposing the cell to light of suitable wavelength to disrupt the endosomal and lysosomal membranes and release the molecules into the cytosol without destroying the functionality of the majority of the cells. Uptake may be facilitated by various carriers. The photosensitizer and the molecule(s) which is (are) to be transported into the cytosol may be conjugated to or applied separately together with suitable carriers, optionally facilitating the uptake of the molecules of interest.

The present invention relates to a method for transporting one or more molecules into the cytosol of a living cell, after which the molecules shall be available in the cytosol and the cell shall maintain its functionability. This is performed by exposing one or more cells to a photoactive compound which is taken up by the cell and will be located in endosomes, lysosomes or other cellular compartments. The photoactive compound is conjugated to or with one or more of a carrier molecule, a targeting immunoglobulin and a molecule to be transported to the cytosol. The cells are then exposed to light of suitable wavelength to activate the photosensitizing compound, such that only the endosomal, lysosomal or other cellular compartment membranes are ruptured, and the molecules are released in the cytosol. Release occurs without the cell losing its functionality by the action of the photoactive compound and possible action of the endosomal/lysosomal content.

The present invention further includes a method for transporting DNA and/or RNA, possibly including one or more genes, via photochemical internalization (PCI) into the cytosol of living cells after which the DNA and/or RNA is available in the cytosol and the cell maintains its functionality. PCI can be used to relocalize DNA and/or RNA oligonucleotides from intracellular granules to the cytosol. The location specificity inherent in the PCI-method can make it possible to specifically deliver DNA and/or RNA to a particular cell type or tissue. For example, PCI can determine nearly exactly to which cell type of an organism the DNA and/or RNA will be delivered and active.

BRIEF DESCRIPTION OF THE DRAWINGS

The present invention is described in detail and illustrated by the accompanying Figures as follows.

DETAILED DESCRIPTION OF THE INVENTION

It is well documented that a number of drugs, including di- and tetrasulfonated aluminum phthalocyanine, sulfonated tetraphenylporphines (TPPS$_n$), nile blue, chlorine$_6$ derivatives, uroporphyrin I, phylloerythrin and possibly hematoporphyrin and methylene blue are located in endosomes and lysosomes of cells in culture. This is in most cases due to endocytic activity. The present invention demonstrates that light exposure of cells containing photosensitizers in their lysosomes leads to a permeabilization of the lysosomes and release of the photosensitizer. In some cases, e.g. TPPS$_{2a}$ and TPPS$_1$, substantial amounts of lysosomal enzyme activities have been found in the cytosol after PDT, indicating that lysosomal contents can be released into the cytosol without losing their activity. This effect of photosensitizing dyes can be used to release endocytosed molecules from endosomes and lysosomes in general according to the present invention.

The introduction of molecules into the cellular cytoplasm is achieved by first exposing the cells or tissue to a photosensitizing dye, the molecule(s) which one wants to deliver into the cytosol of the cells and, optionally, carrier molecules and immunoglobins, all of which should preferentially localize in endosomes and/or lysosomes. Secondly, the cells (or tissue) are (is) exposed to light of suitable wavelengths inducing a photodynamic reaction. This photodynamic reaction will lead to disruption of lysosomal and/or endosomal membranes, and the contents of these vesicles will be released into the cytosol.

Figure 1:
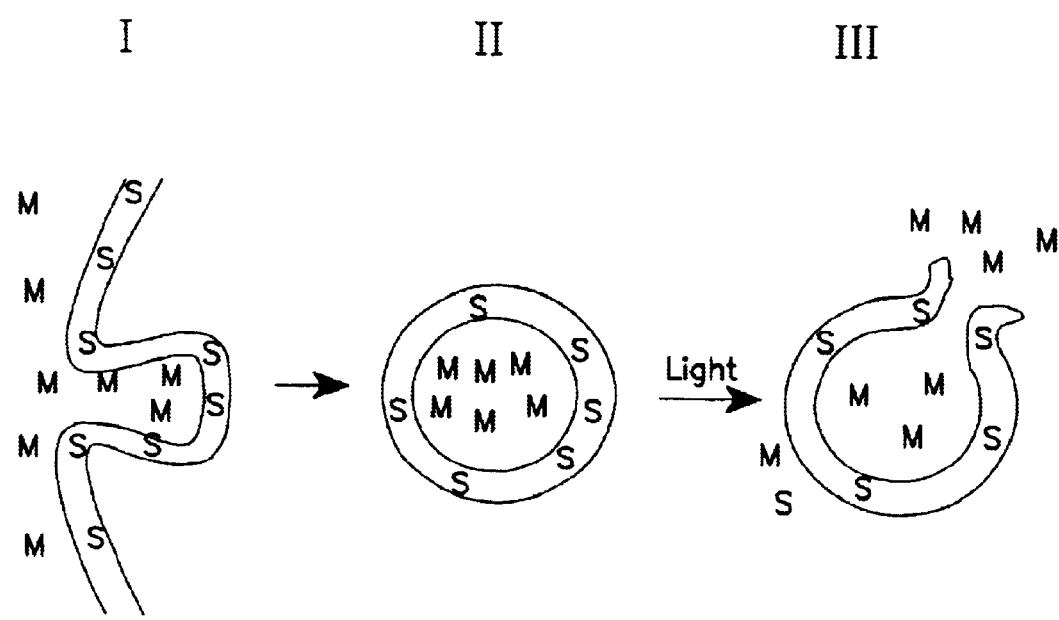
FIG. 1 illustrates a method by which molecules can be introduced into the cellular cytosol by means of the present invention. The photosensitizer (S) and the molecules of choice (M) are endocytosed by the cells (I. illustrates the invagination of the plasma membrane initiating the endocytic process) and both substances end up in the same vesicles (II). When these vesicles are exposed to light, the membranes of the vesicles rupture and the contents are released (III).

The principles of the present invention are illustrated in FIG. 1. It is necessary that the photosensitizer and the molecule to be introduced into the cells are located in the same compartments. It should also be emphasized that externally added molecules may accumulate in intracellular compartments other than lysosomes and endosomes, e.g. Golgi apparatus and endoplasmic reticulum. In such cases, photosensitizing compounds located in the same compartments may in combination with light be used for the same purposes provided that the combination of light doses (irradiation time) and photosensitizing compound does not destroy the functionality of the cells.

The present invention is based on the in vitro demonstration, that a photosensitizer, for example TPPS$_{2a}$ (tetraphenylporphine with 2 sulfonate groups on adjacent phenyl groups) in combination with light can induce release of functionally intact lysosomal contents without killing a large fraction of the cells. The same effect may be obtained by using other photosensitizing compounds alone or associated with/linked to other molecules or particles used as vectors for directing the photosensitizers to endosomes/lysosomes or other intracellular compartments. Such vectors can be tissue or cell specific antibodies or other ligands that bind to the cell surface, thus increasing the uptake of the photosensitizer through receptor-mediated endocytosis. Another vector could be the use of reconstituted LDL-particles. These particles are also taken up by receptor-mediated endocytosis. The number of photosensitizer molecules per LDL particle and the binding to the LDL-particles can in this way be increased compared to prebinding to native LDL.

The present invention is not restricted to in vitro use, but may as well be used in vivo, either by in situ treatment or by ex vivo treatment followed by injection of the treated cells. The uptake into endosomes and lysosomes can be enhanced in the same manner as described above for in vitro treatment.

All tissues can be treated as long as the photosensitizer is taken up by the target cells and the light can be properly delivered.

The present invention is based on both a photosensitizer and light. The light must be absorbed by the photosensitizer or indirectly induce an excited state of the photosensitizer. The wavelength region of use will therefore depend on the photosensitizer. The exposure light does not need to be monochromatic or collimated. Every light source emitting the appropriate wavelengths can be used.

Surprisingly the photodynamic action according to the present investigation seems to neutralize the potentially cytotoxic effect of releasing the lysosomal content. The present authors have thus established that lysosomal cathepsin is substantially inhibited by the photodynamic action of $TPPS_{2a}$ in a culture of NHIK 3025 cells. This was a surprising effect of the present invention and assists in maintaining the viability and functionality of the cells after transporting molecules into cytosol by disrupting endosomal/lysosomal membranes.

Compositions and Methods for Delivery of DNA and/or RNA to the Cytosol of a Cell The invention includes compositions and methods for delivering DNA and/or RNA to the cytosol of a cell. Once in the cytosol of the cell the method or composition can result in expression of a product encoded by the DNA or RNA at a specific cell, tissue, or location in a subject, e.g. in a tumor.

In one embodiment of the invention, a DNA and/or RNA, such as an oligonucleotide, can be provided as or delivered in any of a variety of forms, e.g. as a free molecule, as a polycation complex, or as a complex with a cationic lipid, and be relocalized from an intracellular granule to the cytosol by PCI. Suitable complexes include a complex with polylysine, poly-arginine, or, preferably, with polyethyleneimine. The DNA or RNA can be or encode a plasmid, which can encode a therapeutic or marker protein (e.g. green fluorescent protein), a ribozyme (e.g. a synthetic ribozyme designed against mRNA of the metastasis associated protein cap1), an antisense oligonucleotide, an aptamer, a triplex forming RNA or oligonucleotide, a peptide nucleic acid, an intracellular recombinant antibody, an antiangiogenetic factors, an angiogenetic factor, an anti-inflammatory molecule, or the like. Suitable therapeutic proteins include a suicide enzyme (e.g. Herpes Simplex Virus thymidine kinase, cytidine deaminase, D-amino acid oxidase, and the like); (ii) a toxin or a part of a toxins (e.g. diphtheria toxin, diphtheria toxin A-chain, ricin, gelonin, and the like); (iii) a recombinant immunotoxin; (iv) a cytokine (e.g. tumor necrosis factor-α, transforming growth factor-β, interleukin-12 and other interleukins, colony-stimulating factors, chemokines and the like); an immunostimulatory molecule (e.g. HLA-B7, B7. 1 costimulatory protein and the like).

The photosensitizer can be chosen as described herein above. Suitable photosensitizers include a porphyrin, a phtalocyanine, a purpurin, a chlorin, a benzoporphyrin, a napthalocyanine, a cationic dye, a tetracycline, or a lysosomotropic weak base or derivative thereof; preferably a porphyrin, a phtalocyanine, a purpurin, a benzoporphyrin, a napthalocyanine, a cationic dye, a tetracycline, or a lysosomotropic weak base or derivative thereof. Preferred photosensitizers include $AlPcS_{2a}$ and $TPPS_{2a}$. In certain cases the effect of PCI increased with increasing photosensitizer concentration. Preferably the photosensitizer accumulates preferentially in tumors.

The method and compositions of the invention can target a variety of cell types, particularly tumor cells. For example, targeted cells include baby hamster kidney (e.g. BHK-21) cells, human colon cancer (e.g. HCT116) cells, a human melonoma cell, and the like.

The uptake and activation of the composition of the invention, typically employing the method of the invention, can be very localized and precise. For example, activation can be absent in cells that are not exposed or shielded from light. In an area exposed to light, a high percentage of cells can, typically, be activated. This clearly illustrates the potential of using PCI to obtain location specific expression of a therapeutic protein in vivo. Both photosensitizer and DNA or RNA can be taken into tumor cells in vivo in such a way that light treatment can lead to a light-dependent and site-specific "activation" of therapeutic genes in vivo. In the method of the invention and the composition of the invention provide for PCI light treatment that can be used to turn on the expression of a therapeutic DNA at a specific location in the body, e.g. in a tumor. For many kinds of putative therapeutic DNA such site specific expression can be very advantageous, since expression of a therapeutic DNA outside the diseased area often can give very severe side effects.

Situations for Experimental and Clinical Utilization

1) Cancer treatment

Several photosensitizers accumulate preferentially in neoplastic tissues, the selectivity for a tumor over the surrounding tissue being usually a factor of 2–3, but this factor may in some cases, such as for brain tissues, be higher, i.e. up to 30. Molecules which may be of clinical interest for treatment of cancer, but are restricted by low or zero uptake into the cytosol can be introduced into the cytosol by means of the present invention. Gelonin, as exemplified below, is an example of such a molecule. Several other molecules, either alone or linked to other molecules (e.g. antibodies, transferrin, photosensitizers, apoB on reconstituted LDL-particles) can be used. Such a combination treatment has several advantages. Namely, it provides enhanced cytotoxic effect in deeper layers of the tumor tissues because low and subtoxic doses of light are sufficient for disruption of lysosomes and endosomes. Furthermore, this combination treatment enhances specificity of the toxin because PDT is only given to the area of tumor localization.

2) Gene therapy

Gene therapy, i.e. the therapeutic transfer of genes to a patient's cells, is promising as a method for treating many genetic disorders such as cancer, cystic fibrosis, cardiovascular diseases and many other diseases. The main problem today is the transfection which must occur in vivo or in some cases can be performed ex vivo. Today, the most frequently used vector, i.e. the structure that helps delivering the DNA molecules into the cells, is different types of viruses, especially retro- and adenoviruses. The drawbacks of such methods are low stability of the vector, limited specificity, low yield and introduction of virus-DNA into human cells.

DNA, either as antisense DNA or whole genes, can be introduced into cells by the aid of photochemically induced disruption of endosomes and/or lysosomes. The treatment can be performed in vivo.

3) Experimental utilization

The present invention can be used to introduce a wide variety of molecules into cells in culture, e.g., genes, antibodies, manipulated proteins and compounds usually not permeable to the plasma membrane.

The present invention is further illustrated by the following non-limiting examples.

EXAMPLES

Example 1

This example demonstrates that photodynamic treatment releases a protein synthesis inhibiting compound into the cytosol.

A number of plant toxins kill cells by entering the cytosol and enzymatically deactivating the ribosomal function. The most cytotoxic plant proteins consist of two polypeptide chains, A and B, linked together by disulfide bridges. The function of chain B is to bind the protein to the surface of the cells, while chain A contains the enzymatic activity. Gelonin is a plant toxin which efficiently inhibits protein synthesis in cell-free systems, but has little or no effect on intact cells. The low cytotoxic effect on intact cells is probably due to the lack of a B chain in gelonin.

Figure 2:
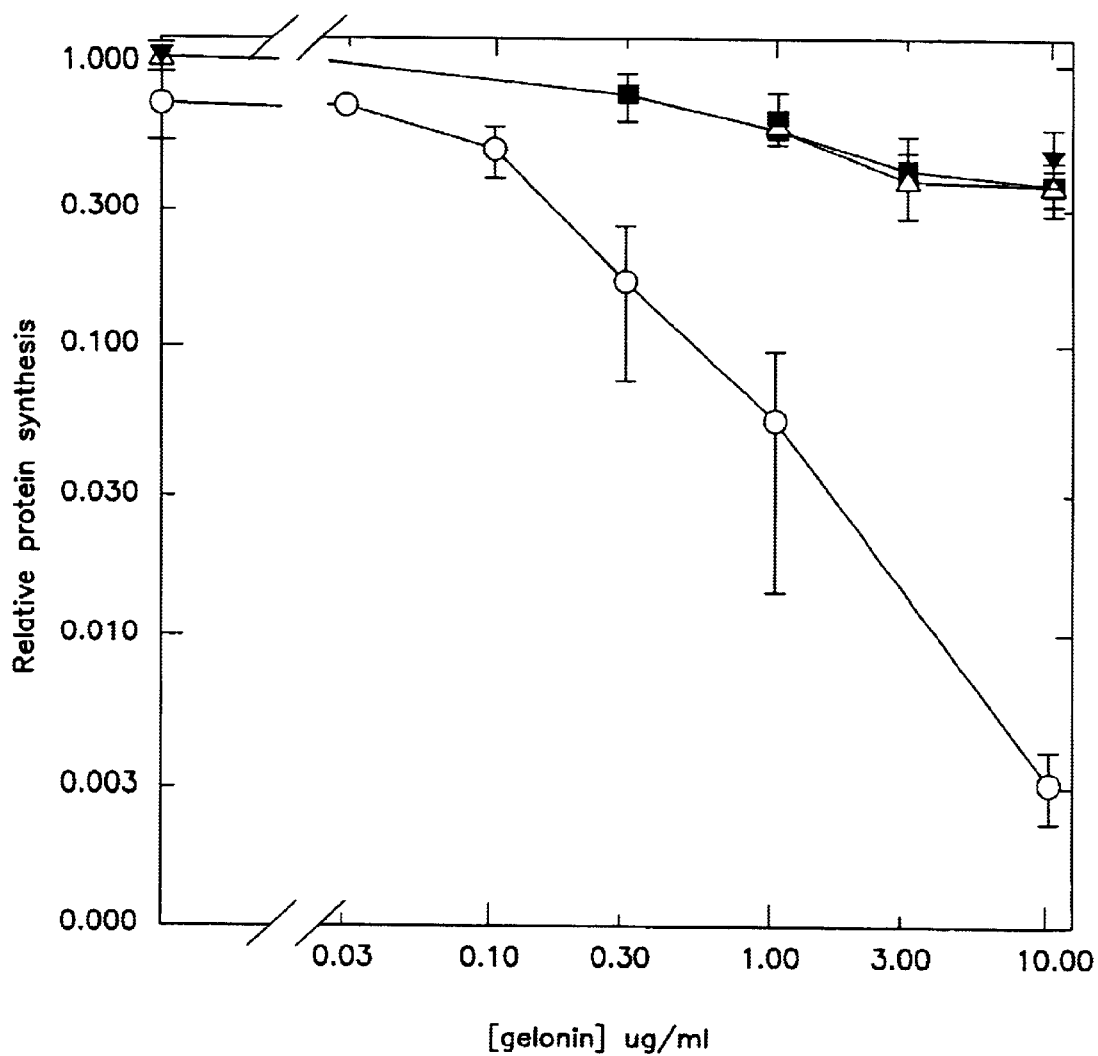
FIG. 2 illustrates protein synthesis in NHIK 3025 cells after treatment with gelonin in the absence or presence of $TPPS_{2a}$ and 50 sec light exposure. Symbols: ○, $TPPS_{2a}$+light; ●, –$TPPS_{2a}$–light; ▽, +$TPPS_{2a}$–light; ▼, –$TPPS_{2a}$+light. The cells were treated with 3.2 µg/ml $TPPS_{2a}$ and the indicated concentration of gelonin overnight and in all cases given the same dose of light. Protein synthesis was measured by measuring incorporation of $^3$[H]leucine into proteins, 24 hours after light exposure.

NHIK 3025 cells were incubated with $TPPS_{2a}$ (Formula I) and gelonin, separately or together for 18 hours, followed by 1 hour in $TPPS_{2a}$ and gelonin-free medium before the cells were exposed to light. Protein synthesis was measured 24 hours after exposure to light. The photodynamic treatment, which kills 10–20% of the cells alone, reduced the protein synthesis by 30–40% (FIG. 2). As seen in FIG. 2, gelonin alone in either the presence or absence of light inhibits protein synthesis to some extent. However, protein synthesis can be completely inhibited by combining PDT and gelonin with an $IC_{50}=0.2$ μg/ml gelonin. Thus, in the absence of the photodynamic treatment, the gelonin essentially did not enter cytosol. This example indicates that $TPPS_{2a}$ and light can be used to introduce functionally intact macromolecules into the cellular cytosol.

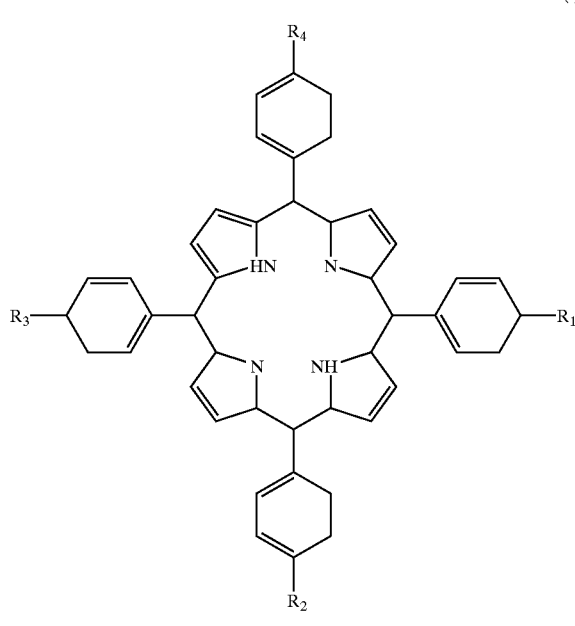

(I)

| $TPPS_4$: $R_{1-4} = SO_2^-$ |
| $TPPS_{2o}$: $R_{1,3} = SO_2^-$ $R_{2-4} = H$ |
| $TPPS_{2a}$: $R_{1,2} = SO_2^-$ $R_{2-4} = H$ |
| $TPPS_1$: $R_1 = SO_1^-$ $R_{2-4} = H$ |

Example 2

This example illustrates how the dose of light (with a wavelength which is absorbed by the dye) can be used to determine the size of the surviving cell fraction.

NHIK 3025 cells were incubated with $TPPS_{2a}$ and gelonin according to the design of Example 1.

Figure 3:
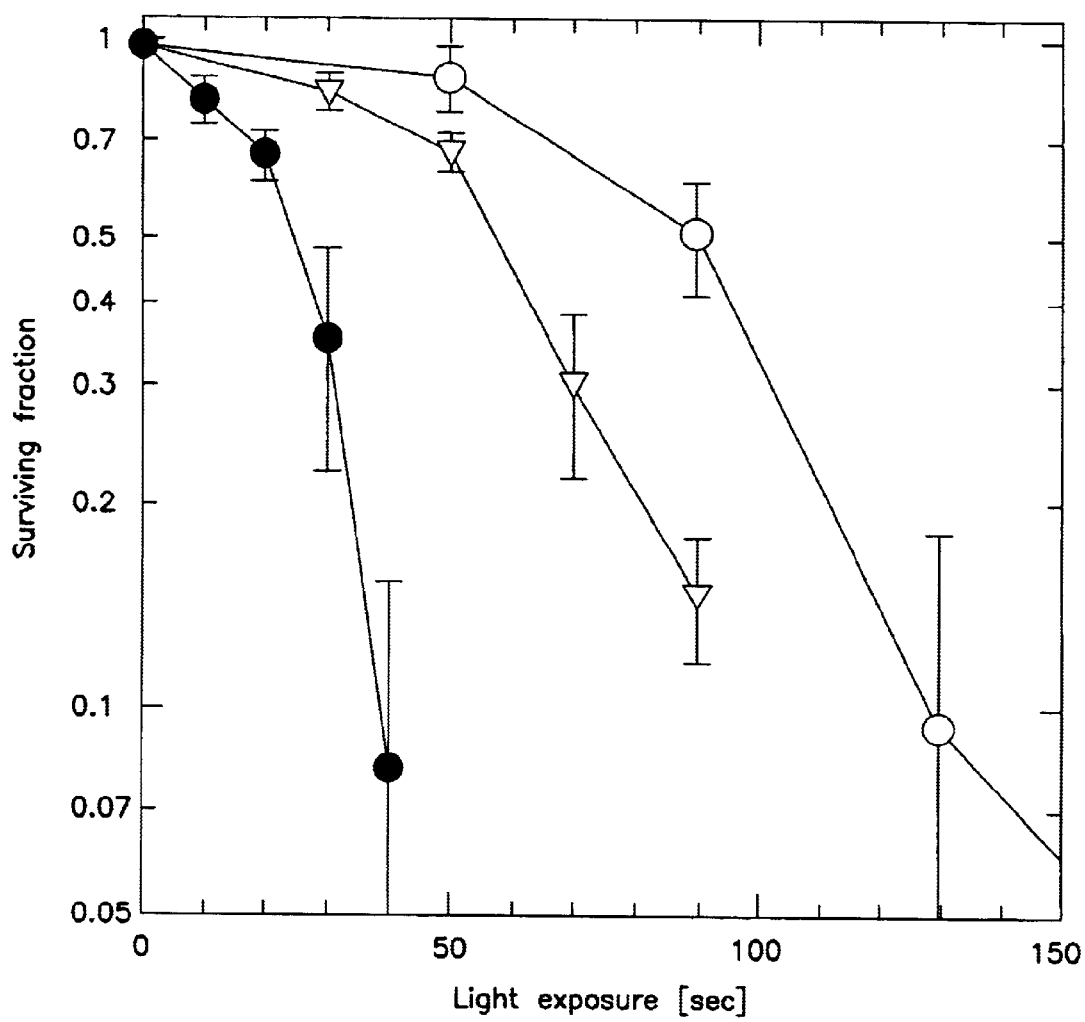
FIG. 3 shows dose-response curves for cells treated with $TPPS_{2a}$ and light only (○) or in combination with 0.2 µg/ml (▽) or 2.0 µg/ml gelonin as described in FIG. 2.

Clonogenic survival of the cells was measured 24 hours after exposure to light. As illustrated in FIG. 3, virtually all cells were killed with $TPPS_{2a}$ and light when the light exposure was increased. This is in accordance with prior art regarding killing unwanted cells with PDT. When gelonin is added, the survival rate drops due to the inhibiting effect of gelonin on protein synthesis, showing that gelonin now is released in the cytosol. Increased concentration of added gelonin leads to more gelonin in the cytosol, as indicated by an increased sensitivity of the cells to photoactivation.

The present invention thus facilitates the determination of the level of survival in each case via selection of the combination of a photosensitizing compound and light exposure which will keep the wanted fraction of cells alive.

Example 3

This example illustrates how changing the light dose (irradiation time) controls the amount of gelonin released in the cytosol, as determined by the relative protein synthesis.

NHIK 3025 cells were incubated with $TPPS_{2a}$ and gelonin according to the design of Example 1.

Figure 4:
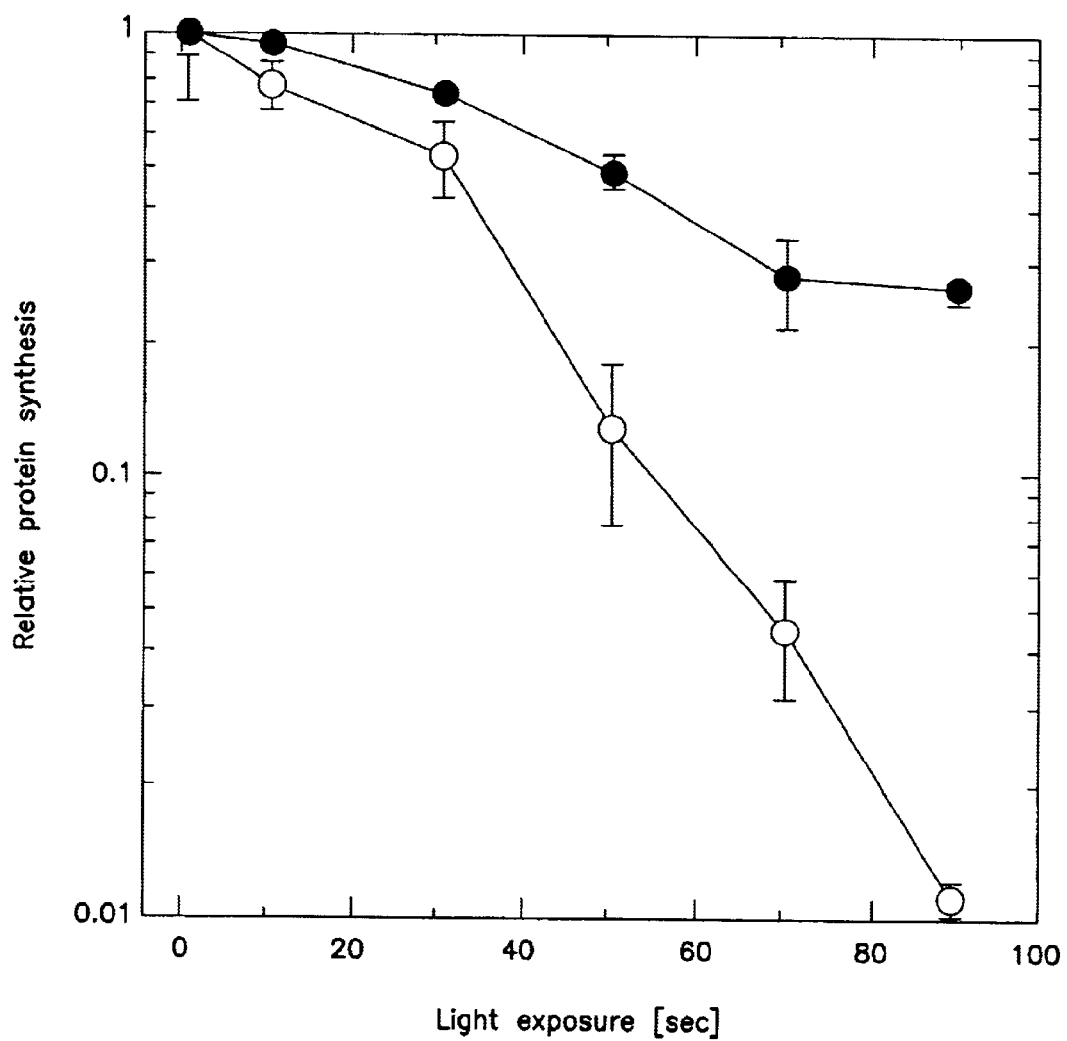
FIG. 4 shows protein synthesis in NHIK 3025 cells after treatment with 3.2 µg/ml $TPPS_{2a}$ and light in the absence or presence of 0.2 µg/ml gelonin. Symbols: ●, $TPPS_{2a}$–gelonin; ○, $TPPS_{2a}$+gelonin. The cells were treated with $TPPS_{2a}$ in the absence or presence of gelonin overnight and exposed to the indicated doses of light. Protein synthesis was measured by measuring incorporation of $^3$[H]leucine into proteins.

FIG. 4 shows that light doses above the toxic dose of 50 seconds increased the gelonin fraction in cytosol as determined by the relative protein synthesis.

Examples 4–11

Examples 4–11 demonstrate use of the method according to the invention on different cell lines and with different photosensitizers and toxins. The intracellular location of the photosensitizers are lysosomal ($TPPS_4$, $TPPS_{2a}$, $AlPcS_{2a}$) and extralysosomal (3-THPP). The following abbreviations are used: $AlPcS_{2a}$ for aluminum phtalocyanine with 2 sulfonate groups on adjacent phenyl rings; $TPPS_4$ for meso-tetraphenylporphine with 4 sulfonate groups; $TPPS_{2a}$ for meso-tetraphenylporphine with 2 sulfonate groups on adjacent phenyl rings; 3-THPP for tetrahydroxylphenyl porphine. The cell lines used were carcinoma cells in situ from human cervix (NHIK 3025), Chinese hamster lung fibroblasts (V79), SV40-transformed African Green monkey kidney (CV1-simian fibroblasts-like cells) (Cos-7) human osteosarcoma cells (OHS) and small cell lung cancer cells (H146). All experiments were designed as in Example 1.

Example 4

Figure 5:
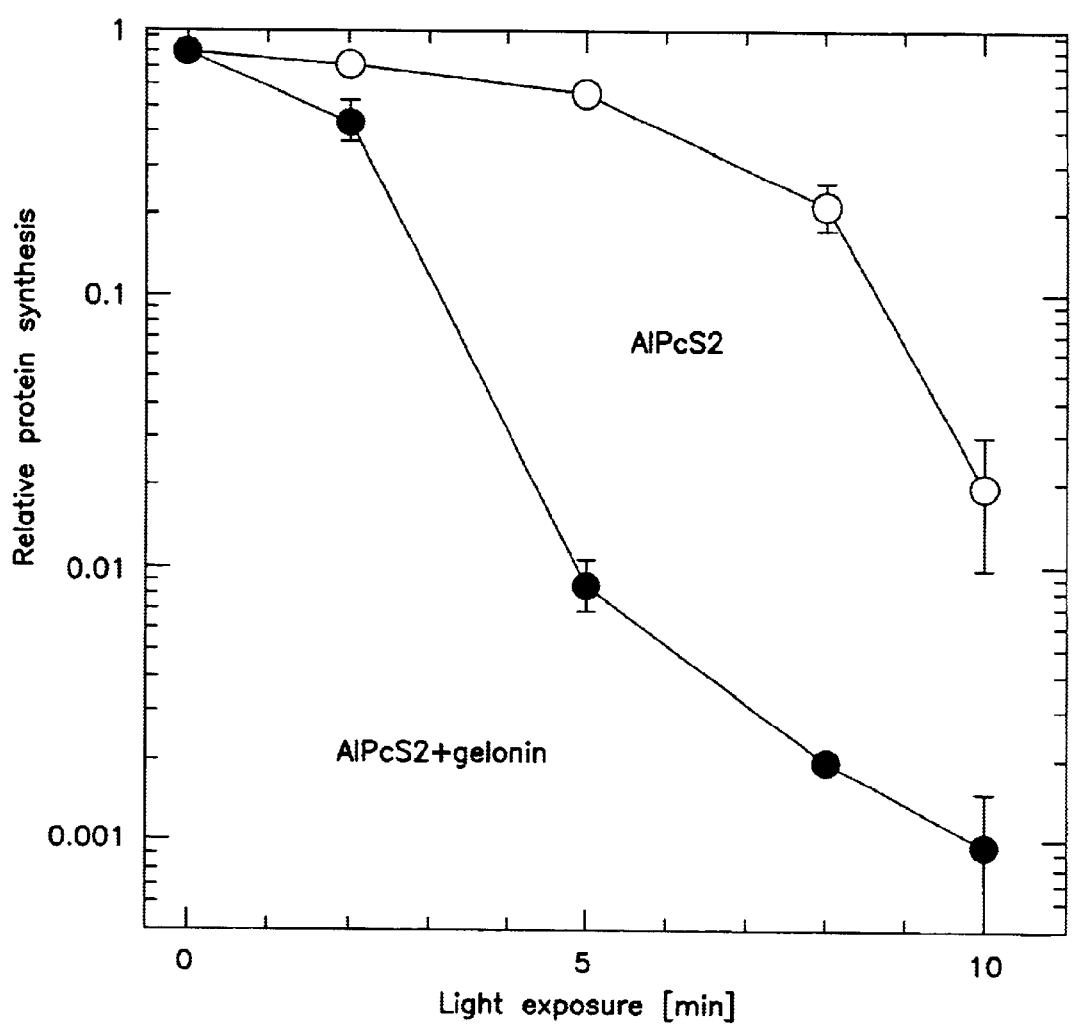
FIG. 5 illustrates protein synthesis in V79 cells after treatment with 25 µg/ml $AlPcS_2$ and light in the absence and presence of 1 µg/ml gelonin. Symbols: ● Photosensitizer+toxin; ○ photosensitizer.

This example relates to use of the photosensitizer $AlPcS_{2a}$ in V79 cells with or without gelonin as the toxin (FIG. 5). By selecting a specific light dose (irradiation time), it is demonstrated that, very little cell damage is produced without the toxin, as illustrated by the small reduction in protein synthesis, while with gelonin the protein synthesis is profoundly reduced. This shows the transport of gelonin molecules into cell cytoplasma via lysosomes without essentially damaging the cells even though the intracellular localization of $AlPcS_{2a}$ is lysosomal. (Moan, J., Berg, K., Anholt, H. and Madslien, K. (1994). Sulfonated aluminum phtalocyanines as sensitizers for photochemotherapy. Effects of small light doses on localization, dye fluorescence and photosensitivity in V79 cells. Int. J. Cancer 58: 865–870.)

Example 5

Figure 6:
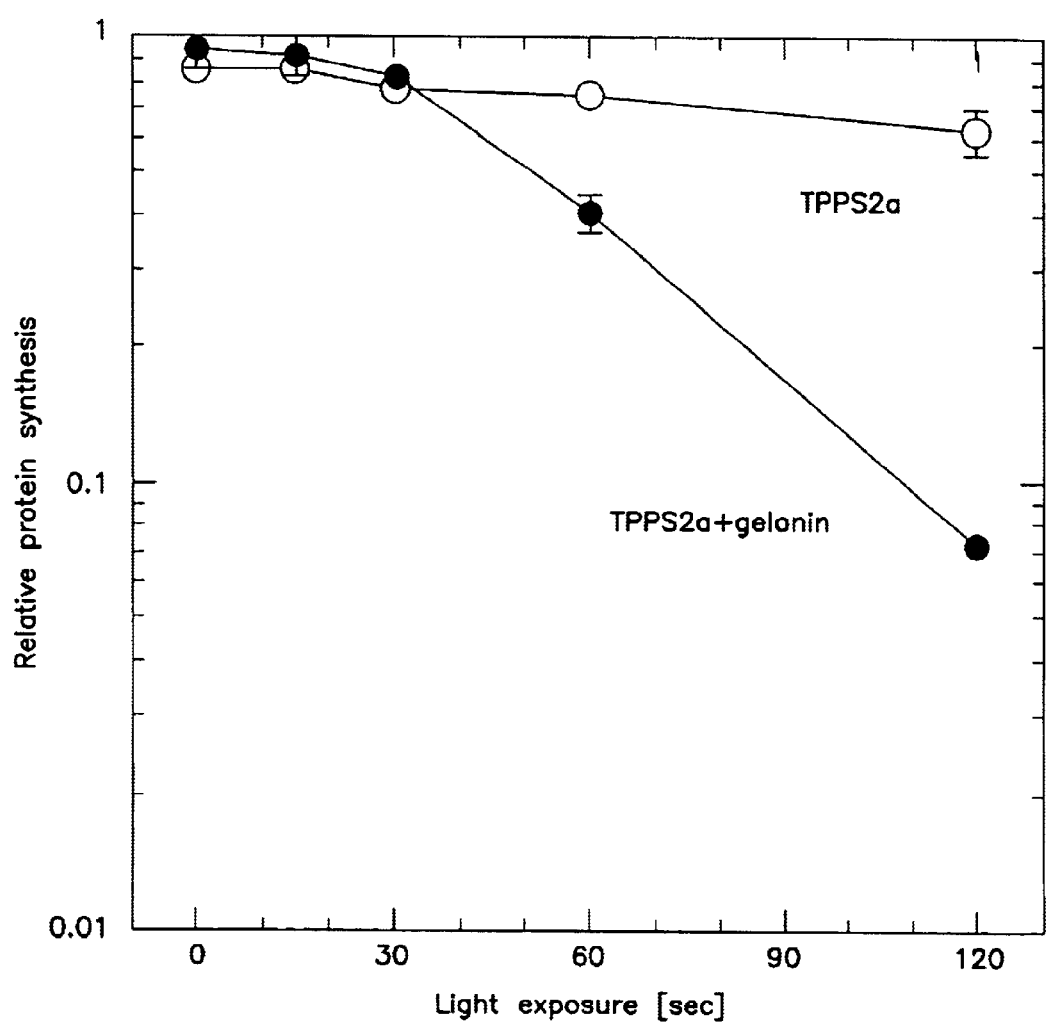
FIG. 6 illustrates protein synthesis in H146 cells after treatment with 0.3 µg/ml $TPPS_{2a}$ and light in the absence and presence of 1 µg/ml gelonin. Symbols as in FIG. 5.

This example demonstrates transport of the toxin gelonin into H146 cells without essentially affecting the viability of the cells. (FIG. 6). $TPPS_{2a}$ is known to be lysosomally located in the cell. (Berg, K., Western, A., Bommer, J. and Moan, J. (1990) Intracellular localization of sulfonated meso-tetraphenylporphines in a human carcinoma cell line. Photochem. Photobiol. 52:481–487; Berg, K., Madslein, K., Bommer J. C., Oftebro, R., Winkelman, J. C. and Moan, J. (1991). Light induced relocalization of sulfonated mesotetraphenylporphines in NHIK 3025 cells and effects of dose fractionation. Photochem. Photobiol. 53:203–210; Berg, K. and Moan, J. (1994) Lysosomes as photochemical targets. Int. J. Cancer. 59:814–822.)

Example 6

Figure 7:
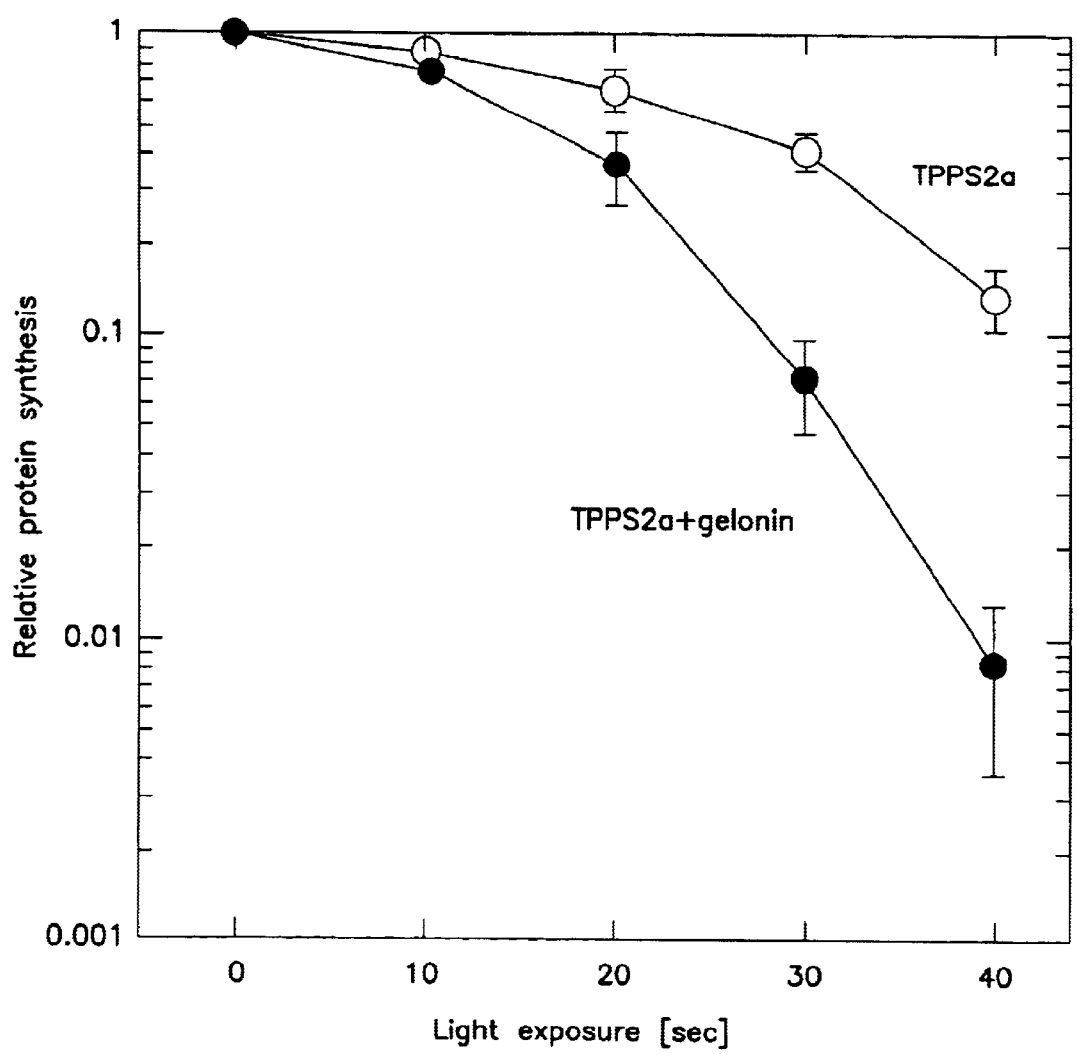
FIG. 7 illustrates protein synthesis in V79 cells after treatment with 1 µg/ml $TPPS_{2a}$ and light in the absence and presence of 1 µg/ml gelonin. Symbols as in FIG. 5.

This example demonstrates the method according to the invention in V79 cells using $TPPS_{2a}$ as photosensitizer (FIG. 7).

Example 7

Figure 8:
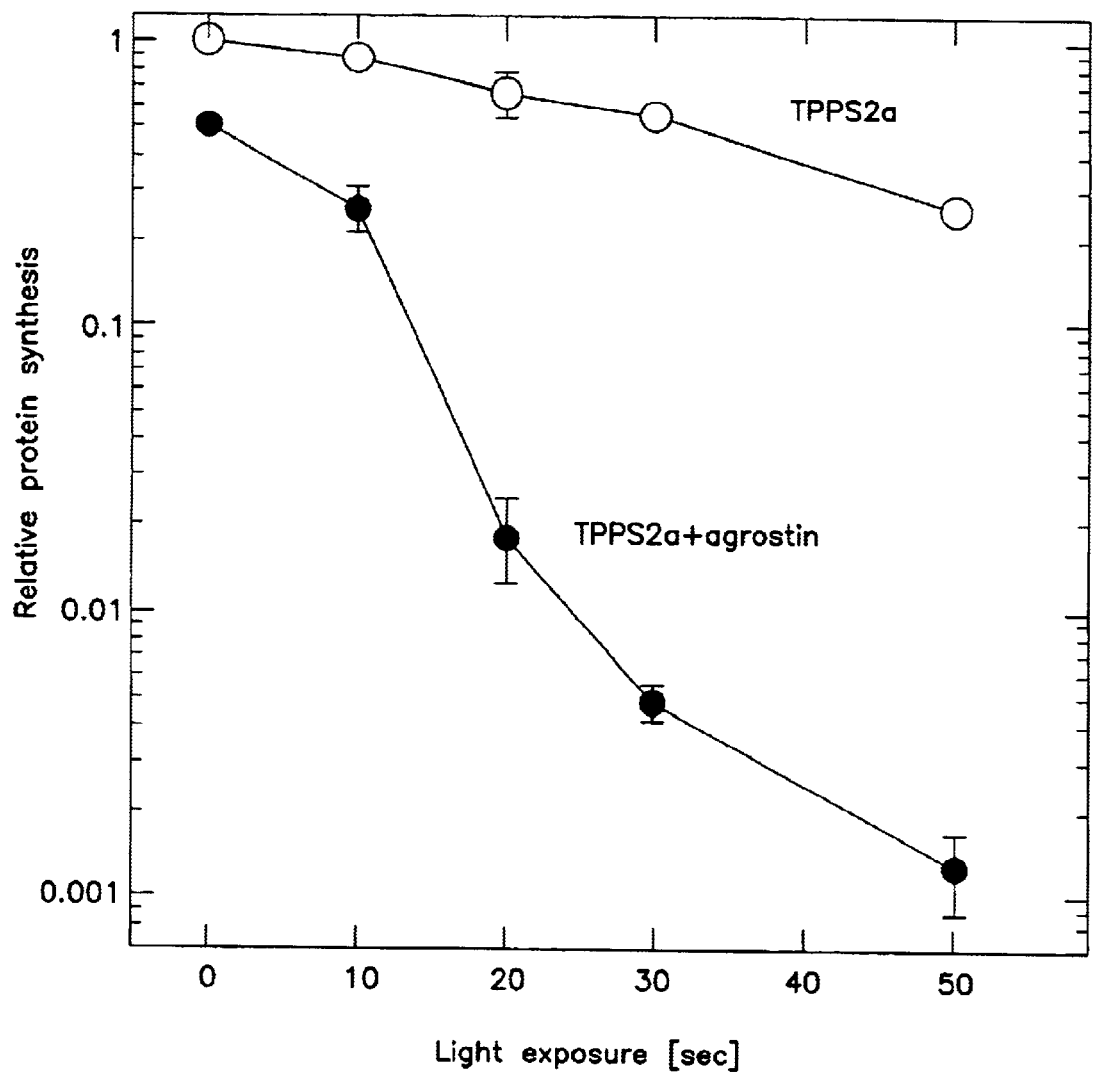
FIG. 8 illustrates protein synthesis in NHIK3025 cells after treatment with 3.2 µg/ml $TPPS_{2a}$ and light in the absence and presence of 1 µg/ml agrostin. Symbols as in FIG. 5.

This example demonstrates transport into NHIK 3025 cells of the toxin agrostin using the photosensitizer $TPP_{2a}$ (FIG. 8).

Example 8

Figure 9:
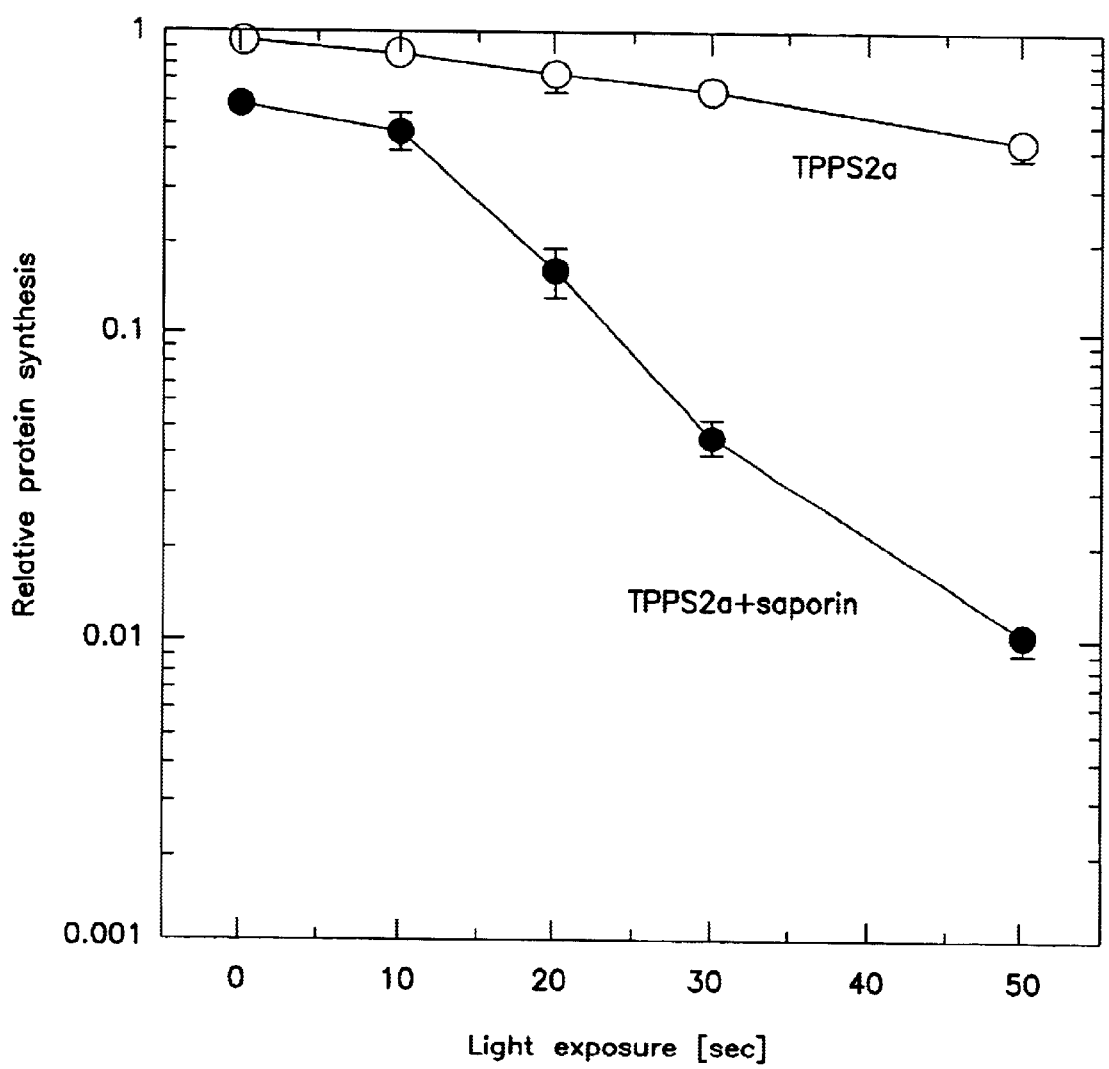
FIG. 9 illustrates protein synthesis in NHIK3025 cells after treatment with 3.2 µg/ml $TPPS_{2a}$ and light in the absence and presence of 1 µg/ml saporin. Symbols as in FIG. 5.

This example demonstrates transport of the toxin saporin into NHIK 3025 cells using $TPP_{2a}$ (FIG. 9).

Example 9

Figure 10:
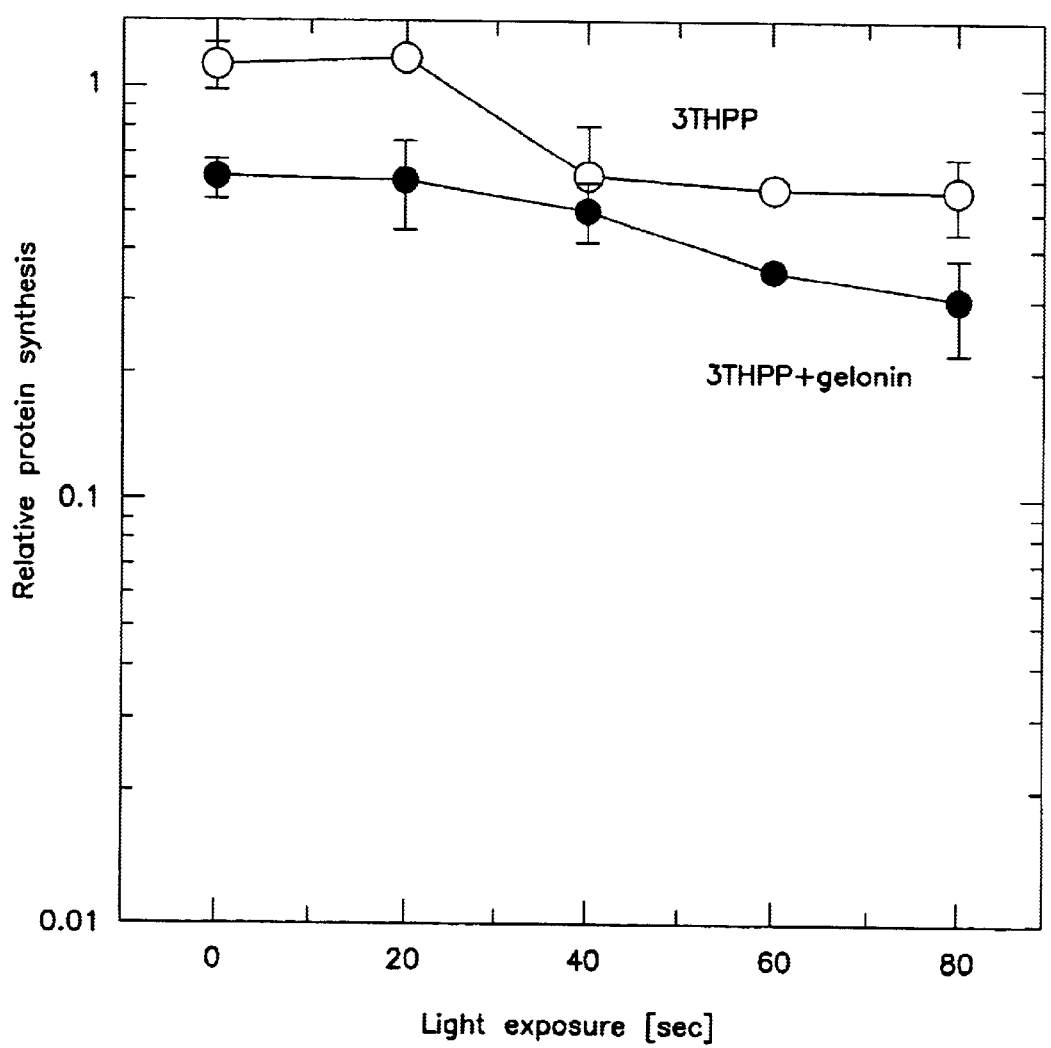
FIG. 10 illustrates protein synthesis in NHIK3025 cells after treatment with 0.25 µg/ml 3-THPP and light in the absence and presence of 1 µg/ml gelonin. Symbols as in FIG. 5.

This is a comparative example demonstrating that when a photosensitizer (3-THPP) which does not enter endocytic vesicles (i.e. endosomes and lysosomes) (Peng, Q., Danielson, H. E. and Moan, J. (1994) Potent photosensitizers for photodynamic therapy of cancer: Applications of confocal laser scanning microscopy for fluorescence detection of photosensitizing fluorophores in neoplastic cells and tissues. In: Proceedings of Microscopy, Holography, and Interferometry in Biomedicine. SPIE Vol. 2083:71–82), there is no significant difference between the protein synthesis effect of 3THPP with or without gelonin (FIG. 10). Thus gelonin is not transported into the cytosol of the cells.

Example 10

Figure 11:
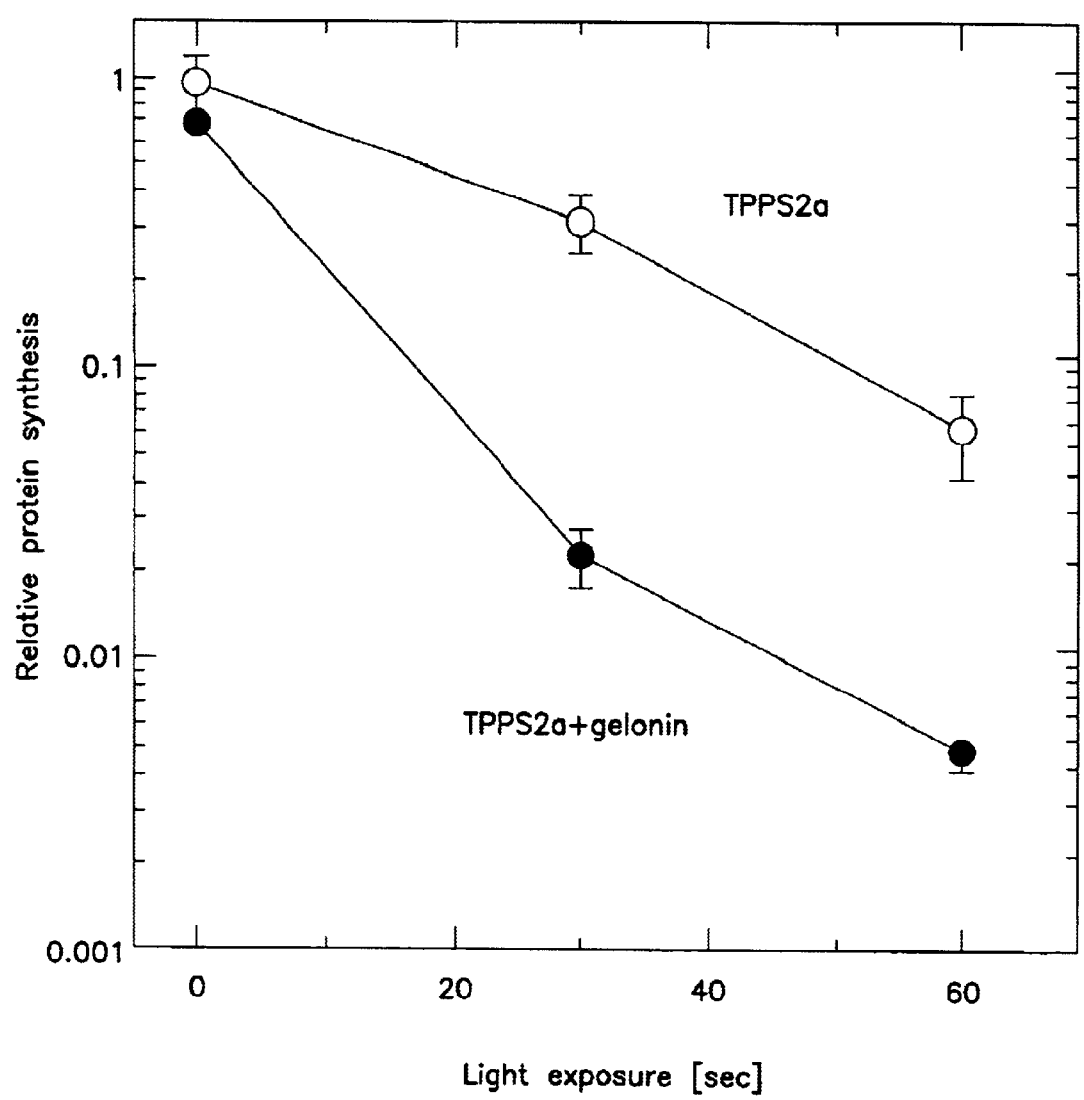
FIG. 11 illustrates protein synthesis in COS-7 cells after treatment with 3 µg/ml $TPPS_{2a}$ and light in the absence and presence of 1 µg/ml gelonin. Symbols as in FIG. 5.

This example demonstrates the transport of gelonin into COS-7 cells by using $TPPS_{2a}$ according to the invention (FIG. 11).

Example 11

Figure 13:
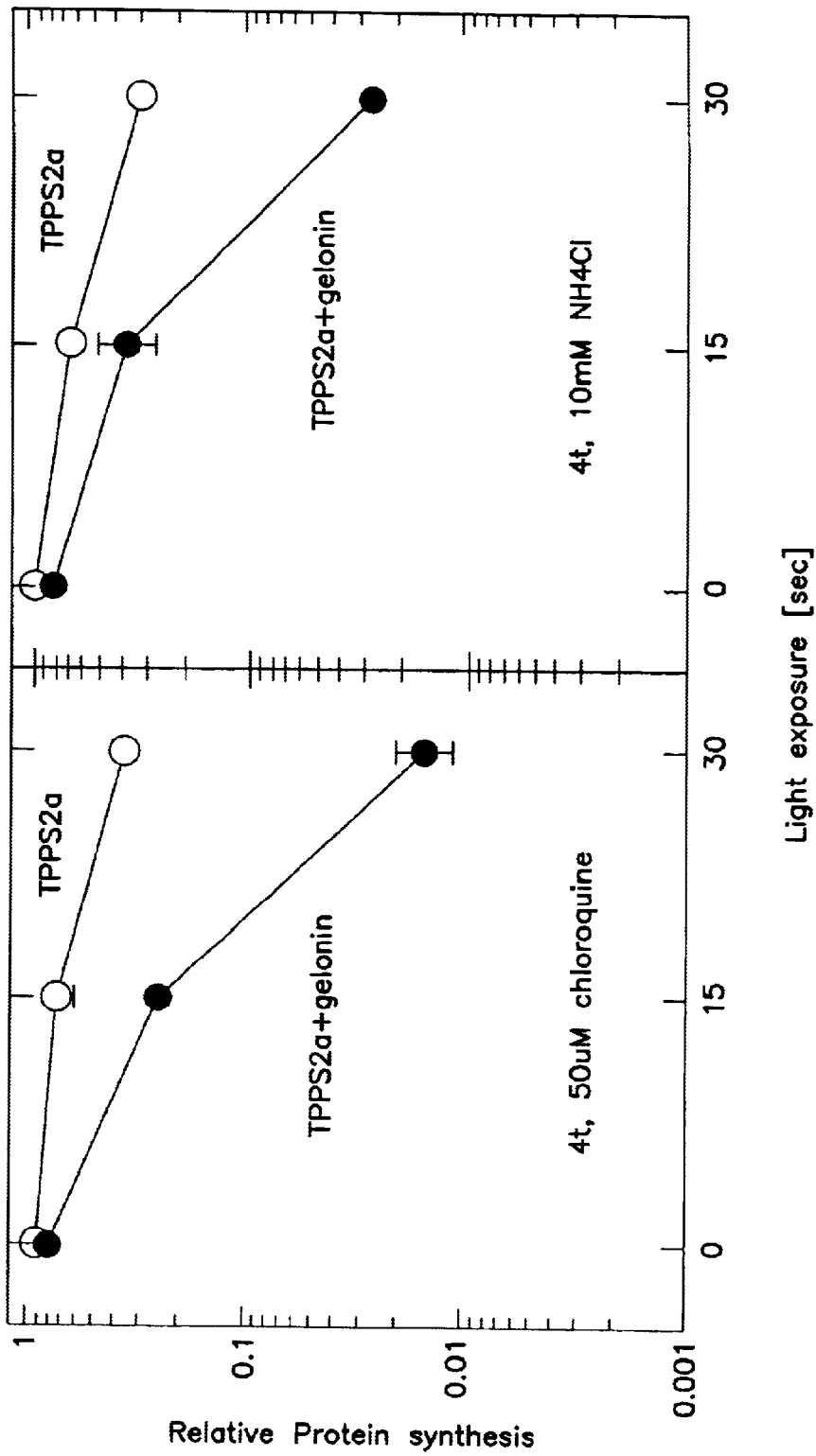
FIG. 13 illustrates protein synthesis in OHS cells after treatment with 3 µg/ml $TPPS_{2a}$ for 18 hours followed by 4 hours in the absence of $TPPS_{2a}$ and in the absence or presence of 3 µg/ml gelonin before exposure to light. The cells were incubated for the same 4 hours in 50 µM chloroquine or 10 mM $NH_4Cl$ to inhibit lysosomal protein degradation.

This example demonstrates the transport of gelonin into OHS cells by using $TPPS_{2a}$ according to the invention. (FIG. 13). In this cell line there is a considerable protein degradation in the lysosomes, which in the present example is inhibited by incubating the cells for 4 hours in either 50 μM chloroquine or 10 mM $NH_4Cl$.

Example 12

Figure 12:
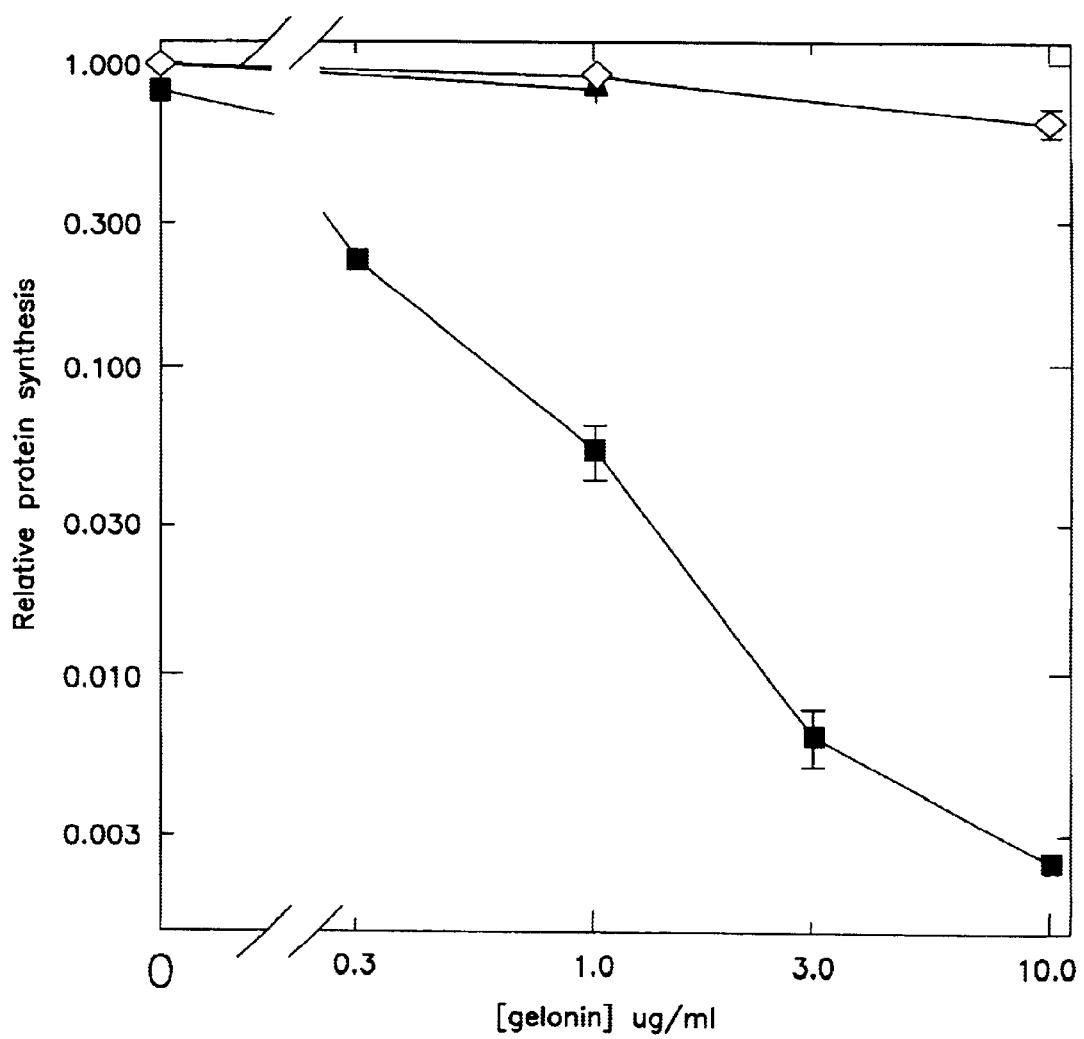
FIG. 12 illustrates protein synthesis in NHIK 3025 cells after treatment with gelonin in the absence or presence of TPPS4 and 50 sec light exposure. Symbols: ■$TPPS_4$+light; ▼–$TPPS_4$–light; ◇ +$RPPS_4$–light. The cells were treated with 75 µg/ml $TPPS_4$ and the indicated concentration of gelonin overnight and in all cases given the same dose of light. Protein synthesis was measured by measuring incorporation of $^3$[H]leucine into proteins, 24 hours after light exposure.

Similar to example 1, this example demonstrates transport of gelonin into NHIK 3025 cells as a function of the gelonin concentration when the cells were incubated with $TPPS_4$ and different concentrations of gelonin and exposed to light (FIG. 12). When the cells were incubated with gelonin alone and exposed to light, or incubated with $TPPS_4$ and gelonin without exposure to light, no transport of gelonin into the cells was obtained.

Conclusions From Examples 1–12

The above described examples demonstrate that different molecules can be introduced into the cells cytosol in a wide variety of cells using different photosensitizers and doses of light. Exogenous molecules can be introduced to the cellular cytosol after doses of photosensitizers and light which do not kill the cells, as long as the molecules to be introduced and the photosensitizers are transported to the same cellular components. The photochemical effect on a biological compartment depends upon the amount of photosensitizers in that compartment, the dose of light applied and the spectral properties of the light source. The best way to evaluate photochemical effects on cells in culture is therefore to measure cell survival 24 hours or more after treatment. There is a good correlation between the effect on cell killing and the inhibition of protein synthesis 24 hours after treatment, as presented above (data not shown).

Example 13—Relocalization of a Fluorescein-Labeled Ribozyme by PCI

Materials and Methods

The ribozyme employed in this example was a 37-mer synthetic 2'-O-methylated ribozyme designed against mRNA of the metastasis associated protein capl. The sequence (SEQ ID NO:1) was as follows:

5'-UAG UUC UCU GAU GAG GCC GNU AGG CCG AAA CUU GUU Y-3', (SEQ ID NO: 1) where N is bases with 2'-O-methylated ribose, Y is uridine with a 3'-3' inverted thymidine at the 3' end, N is fluorescein attached to uracil.

To study the intracellular localization of the photosensitizer $AlPcS_{2a}$ and the ribozyme, THX human melanoma cells were plated on 16 well Lab-Tek (Nunc Inc.) chamber slides (3000 cells well$^{-1}$). After 18 h the culture medium was replaced with fresh RPMI medium supplemented with 10% fetal calf serum (FCS, Integro b.v., Holland) and containing 20 mg/ml $AlPcS_{2a}$ and 5.5 mM ribozyme. After 18 h incubation at 37° C. the medium was replaced with fresh sensitizer-free and ribozyme-free RPMI medium supplemented with 10% FCS, and the cells were incubated for an additional 1 h. The cells were then irradiated for 10 min with red light (Phillips TL 20 W/09, filtered through a Cinemoid 35 filter).

After 40 min unfixed cells were observed with a Zeiss Axioplan fluorescence and phase-contrast microscope (Oberkochen, Germany) using an objective with 40 times magnification. Control cells were observed without irradiation. The microscope was equipped with a 450–490 nm band pass excitation filter for FITC-ribozyme and a 365 nm excitation filter for $AlPcS_{2a}$. Phase-contrast and fluorescence micrographs were recorded by means of a cooled charge-coupled device (CCD) camera (Astromed 3200, Cambridge, England).

Results

Figure 14:
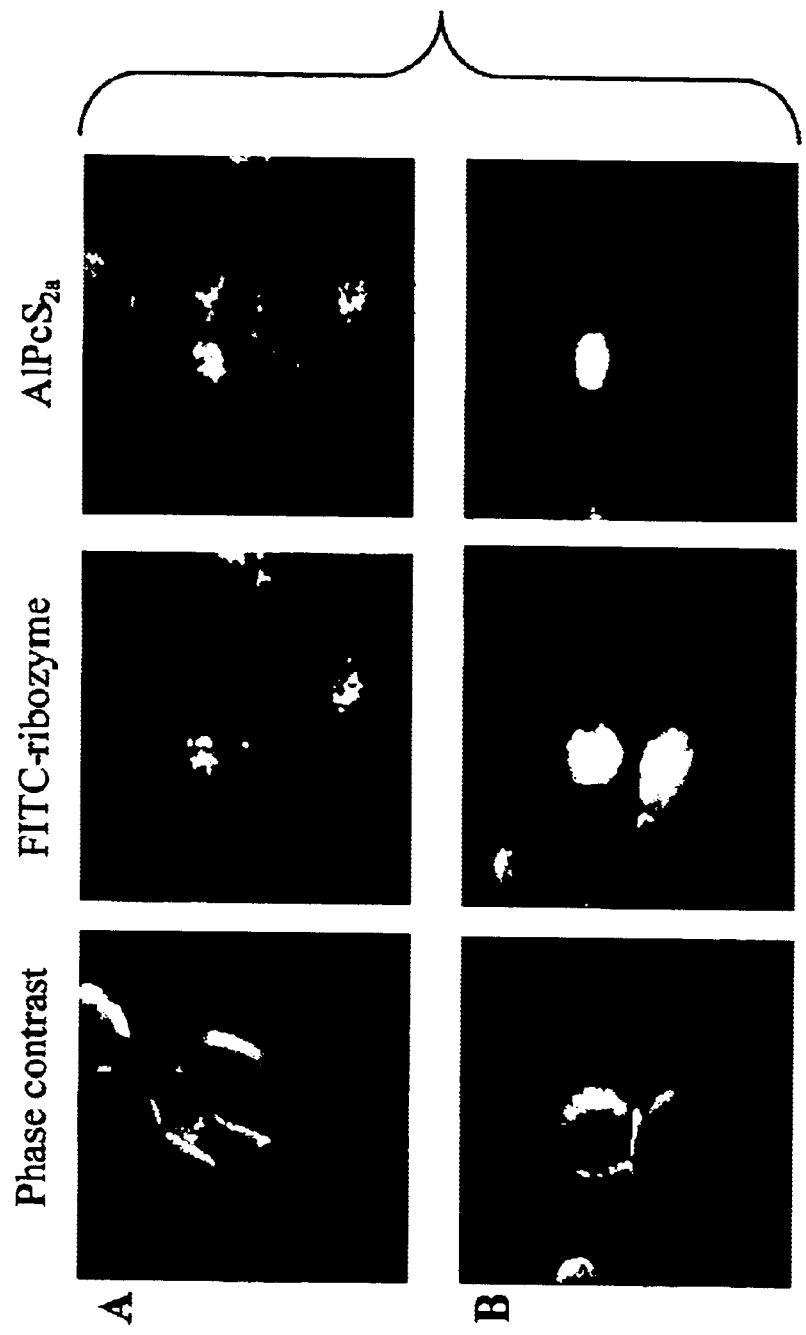
FIG. 14 illustrates subcellular localization of a fluorescein-ribozyme (5.5 µM) and $AlPcS_{2a}$ (20 µg/ml) in THX cells after 18 h incubation followed by 1 h wash. The Figure illustrates localization without light exposure (A) and after 10 min red light exposure followed by 40 min incubation in the dark (B). (Magnification 40×2.5).

As can be seen from FIG. 14 in nonirradiated cells the ribozyme was mainly localized in intracellular granules. After light exposure most of the ribozyme fluorescence was present in the cytosol indicating a PCI-induced relocalization of ribozyme from the granules to the cytosol.

Example 14—PCI Relocalization of an Oligodeoxynucleotide-polylysine Complex

Materials and Methods

The culture medium used under the entire procedure was RPMI containing 2 mM glutamine, 100 U/ml Penicillin and 100 μg/ml Streptomycin (all Bio-Whittaker) and 10% FCS. Cells were cultured in an incubator containing 5% $CO_2$. The oligonucleotide used was a fluorescein-labeled 60 base oligodeoxynucleotide (ODN) (Medprobe) in a stock solution of 100 μM. Polylysine was MW 20700 (Sigma), in a stock solution of 1 mg/ml in water.

An ODN-polylysine complex was formed by gently mixing 1.5 μg ODN in 75 μl 20 mM Hepes buffer (HBS) pH 7.4 with 0.8 μg polylysine in 75 μl HBS (charge ratio: 0.8; the charge ratio is the number of positive charges supplied by the amino groups of polylysine divided by the negative charges provided by the phosphate groups of ODN). After 30 min incubation at room temperature the solution was diluted with culture medium to a final volume of 1 ml and added to the cells (1 ml per well).

100 000 THX-cells were seeded out into a Falcon 3001 dish. After overnight incubation 20 μg/ml AlPcS$_{2a}$ was added and the cells were incubated for 18 h at 37° C. The cells were washed 3 times with culture medium and incubated in sensitizer-free medium for additional 3 h before being transfected with ODN-polylysine complex for 4 h. After transfection the cells were incubated in culture medium for 1.5 h and unfixed cells were observed for the intracellular localization of the ODN and AlPcS2$a$ with fluorescence and phase-contrast microscopy (objective with 40 times magnification, the microscope was equipped with a 450–490 nm band pass excitation filter). For relocalization studies the cells were exposed to microscope light for 10 s and after 1 min (relocalization time) fluorescence pictures were taken.

Results

Figure 15:
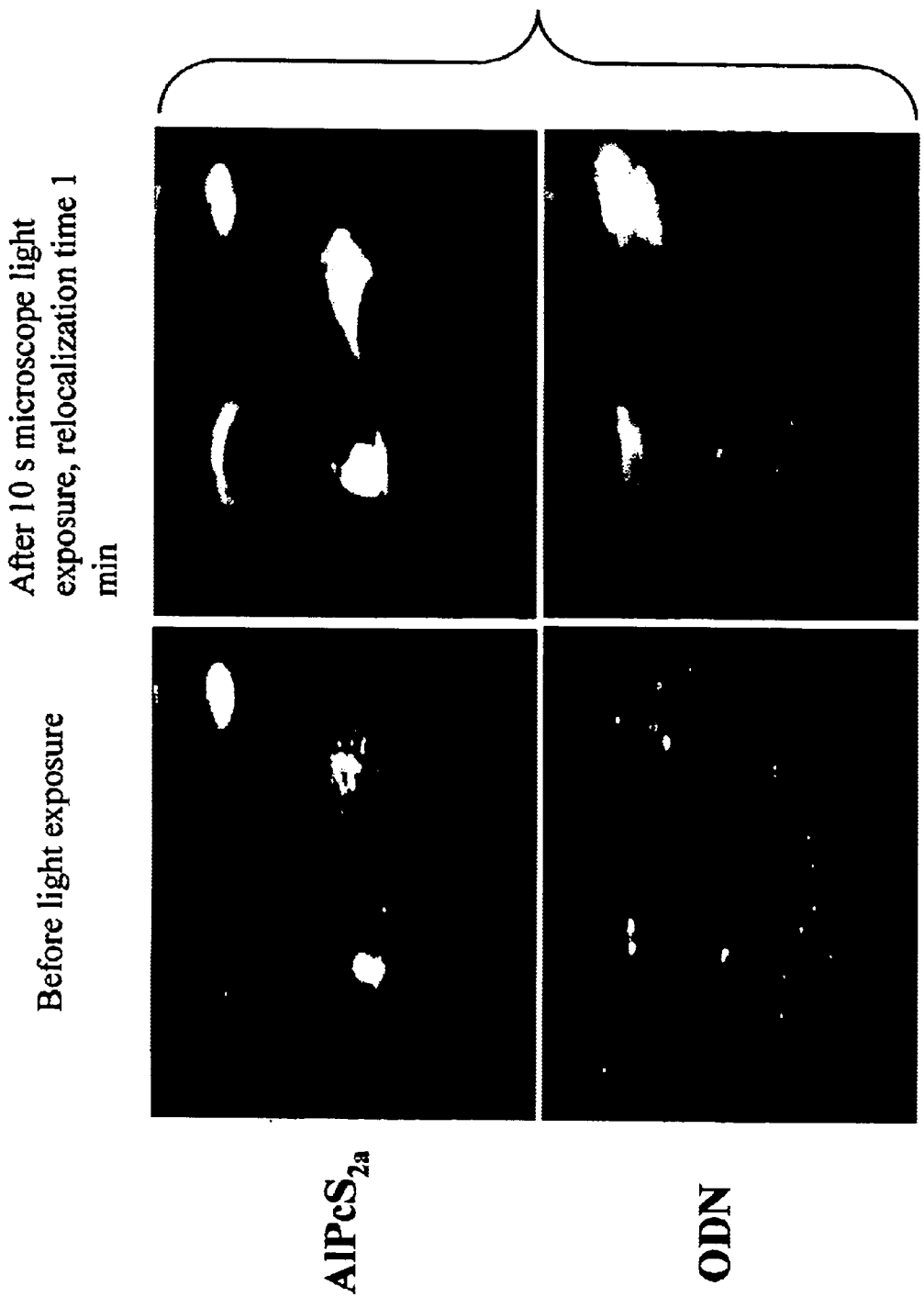
FIG. 15 illustrates PCI relocalization of an oligodeoxynucleotide-polylysine complex in THX-cells that were transfected with a oligonucleotide-polylysine complex and the cells were analysed by microscopy as described in the text of Example 14.

From FIG. 15 it can clearly be seen that the oligonucleotide-polylysine complex is taken up by the cells in such a way that it ends up in intracellular granules (left panels). It is also apparent that the light treatment induced a relocalization of both the photosensitizer and the fluorescein-labeled ODN from the granules into the cytoplasm (right panels).

Example 15—PCI Relocalization of an Oligodeoxynucleotide-DOTAP Complex

Materials and Methods

An ODN-DOTAP (DOTAP is an abbreviation for (N-[1-(2,3-dioleoyloxy) propyl]-N,N,N-trimetylammonium methyl sulphate) complex was formed by gently mixing 5 μg ODN (same as in Example 14) in 42 μl 20 mM Hepes buffer (HBS) pH 7.4 with 25 μg DOTAP (Boehringer Mannheim) in 84 μl HBS (25 μg DOTAP per 5 μg ODN and the volume of ODN mixture is half of the DOTAP mixture volume). After 15 min incubation at room temperature the solution was diluted with culture medium to a final volume of 1 ml and added to the cells (1 ml per well).

100 000 THX-cells were seeded out into a Falcon 3001 dish. After overnight incubation 20 μg/ml AlPcS$_{2a}$ was added and the cells were incubated for 18 h at 37° C. The cells were washed 3 times with culture medium and incubated in sensitizer-free medium for additional 3 h before being transfected with the ODN-DOTAP complex for 4 h. After transfection the cells were incubated in culture medium for 2 h and unfixed cells were observed for the intracellular localization of ODN and AlPcS$_{2a}$ with fluorescence and phase-contrast microscopy (objective with 40 times magnification, the microscope was equipped with a 450–490 nm band pass excitation filter). For relocalization studies the cells were exposed to microscope light for 10 s, and after 1 min (relocalization time) fluorescence pictures were taken.

Results

Figure 16:
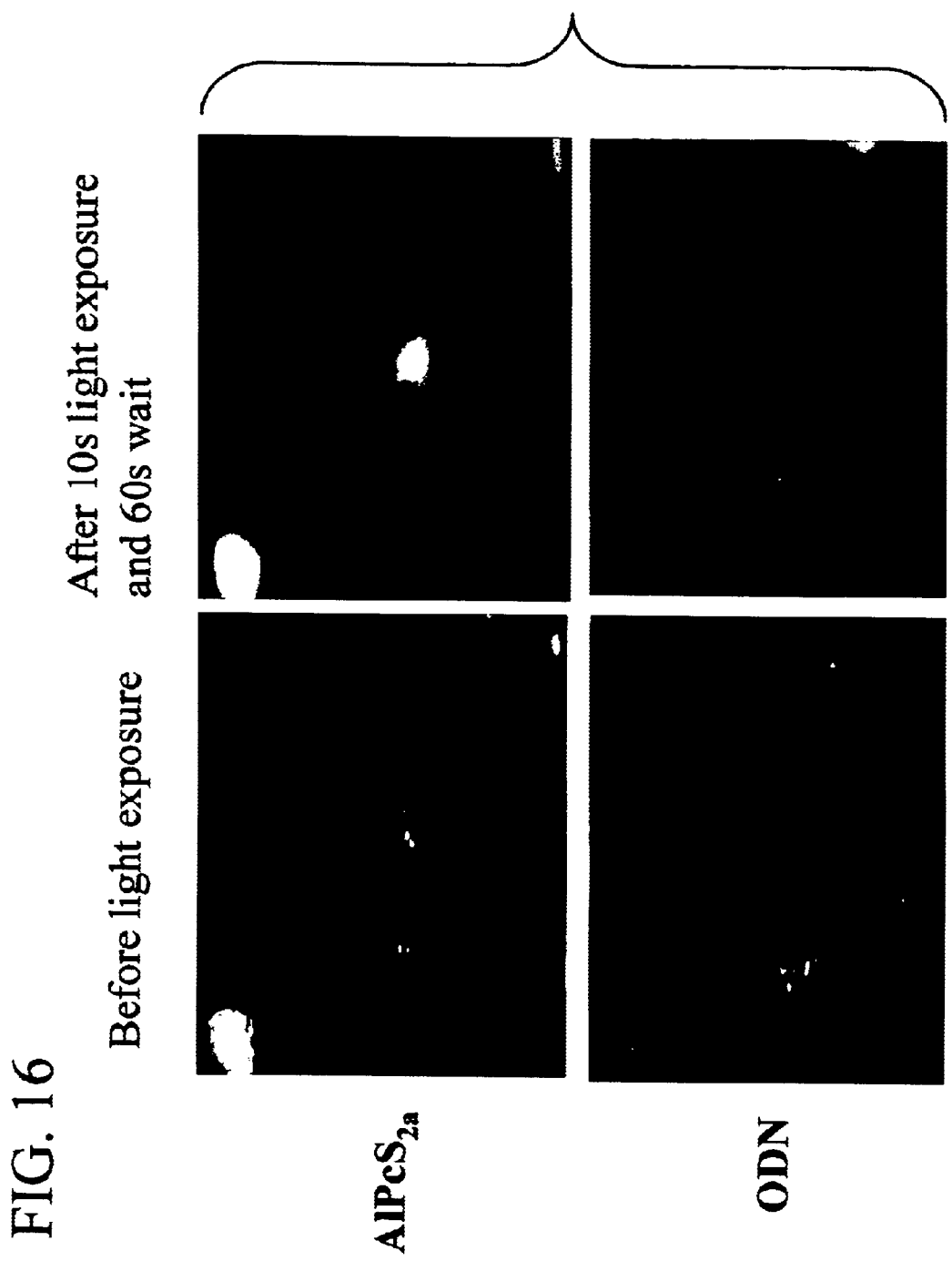
FIG. 16 illustrates PCI relocalization of an oligodeoxynucleotide-DOTAP (DOTAP is an abbreviation for N-[1-(2,3-dioleoyloxy) propyl]-N,N,N-trimetylammonium methyl sulphate) complex in THX-cells that were transfected with a oligonucleotide-DOTAP complex and the cells were analysed by microscopy as described in the text of Example 15.

From FIG. 16 it is evident that the ODN-DOTAP complex is taken up by the cells in such a way that it ends up in intracellular granules (left panels). It is clearly seen that the microscope light treatment induced a relocalization of both the photosensitizer and the fluorescein-labeled ODN from the granules into the cytoplasm (right panels).

Conclusions From Examples 13–15

Examples 13–15 show that oligonuclotides delivered by the most common delivery methods, i.e. as free molecules (Example 13), as a polycation complex (Example 14) or as a complex with a cationic lipid (Example 15), can all be relocalized from intracellular granules to the cytosol by PCI. The examples also show that PCI can be used to relocalize both DNA (Example 14 and 15) and RNA (Example 13) oligonuclotides.

It is well known from the literature that insufficient escape from intracellular vesicles is a major barrier for the biological action of oligonucleotides. Thus, PCI can greatly increase the biological action of an olignuclotide, such as for example a ribozyme, an antisense oligonucleotide, an aptamer, a triplex forming oligonucleotide, a peptide nucleic acid, and the like. Also, the location specificty inherent in the PCI-method can make it possible to determine nearly exactly in which cell type or location in the organism an oligonucleotide will be active. In the treatment of many diseases this can be of great advantage, diminishing unwanted side effects of the oligonucleotide in normal healthy cells or tissues.

Example 16—Relocalization of FITC-ODN after in vivo injection of PLL-complex

This example illustrates relocalization of a fluorescein-labeled oligodeoxynucleotide complex after in vivo injection of AlPcS$_{2a}$ and oligodeoxynucleotide-polylysine complex.

Materials and Methods

Animals and tumor model. Female BALB/c athymic nude mice were 7–8 weeks old and weighed 20–22 g when the experiments started. The human malignant melanoma cell line, THX, was established at The Norwegian Radium Hospital. THX cells grown in vitro were injected subcutaneously into the flank of the mice, and the tumors were propagated by serial transplantation. Injection of drugs started when the tumor volume was about 110 mm$^3$.

Preparation of oligonucleotide-polylysine complex. The oligonucleotide (ODN) was the same as used in Example 14. To get a complex consisting of 30 mg ODN/108 nmol polylysine (charge ratio 1.2, total volume 50 ml) the following amounts were used: 16 ml ODN (1.86 mg/ml) was diluted with 9 ml Hepes buffer (20 mM, pH 7.4) to 25 ml. 23 ml polylysine (1 mg/ml) was diluted with 2 ml Hepes buffer to 25 ml. Both solutions were mixed and incubated at room temperature before the injection.

Injection of AlPcS$_{2a}$ and ODN-polylysine complex. 40 mg/kg AlPcS$_{2a}$ was injected i.p. The mice were kept in a cage covered by aluminum paper for 48 h prior to DNA-injection. ODN-polylysine complex (see above, total volume 50 ml) was injected directly into the center of the tumor. 6 h after injection, the tumor was removed and a single cell suspension was prepared by enzymatic digestion. Shortly, the excised tumor was homogenized with a knife and transferred to an enzyme mixture consisting of 0.2% collagenase (type 1) and 0.05% protease (type XXV) in Hanks' balanced salt solution (HBSS). The enzymatic disaggregation at 37° C. lasted for 1 hr. The cells were then centrifuged at 1000 rpm for 5 min, resuspended in 1 ml of cultivation medium (RPMI), diluted with 9 ml of the medium and filtered through a sterile 30 mm filter.

Isolated cells were seeded out into a Falcon 3001 dish (100 000 cells per dish). 24 hrs later the intracellular localization of FITC-ODN was analyzed by microscopy before and after light treatment as described in Example 14.

Results

Figure 17:
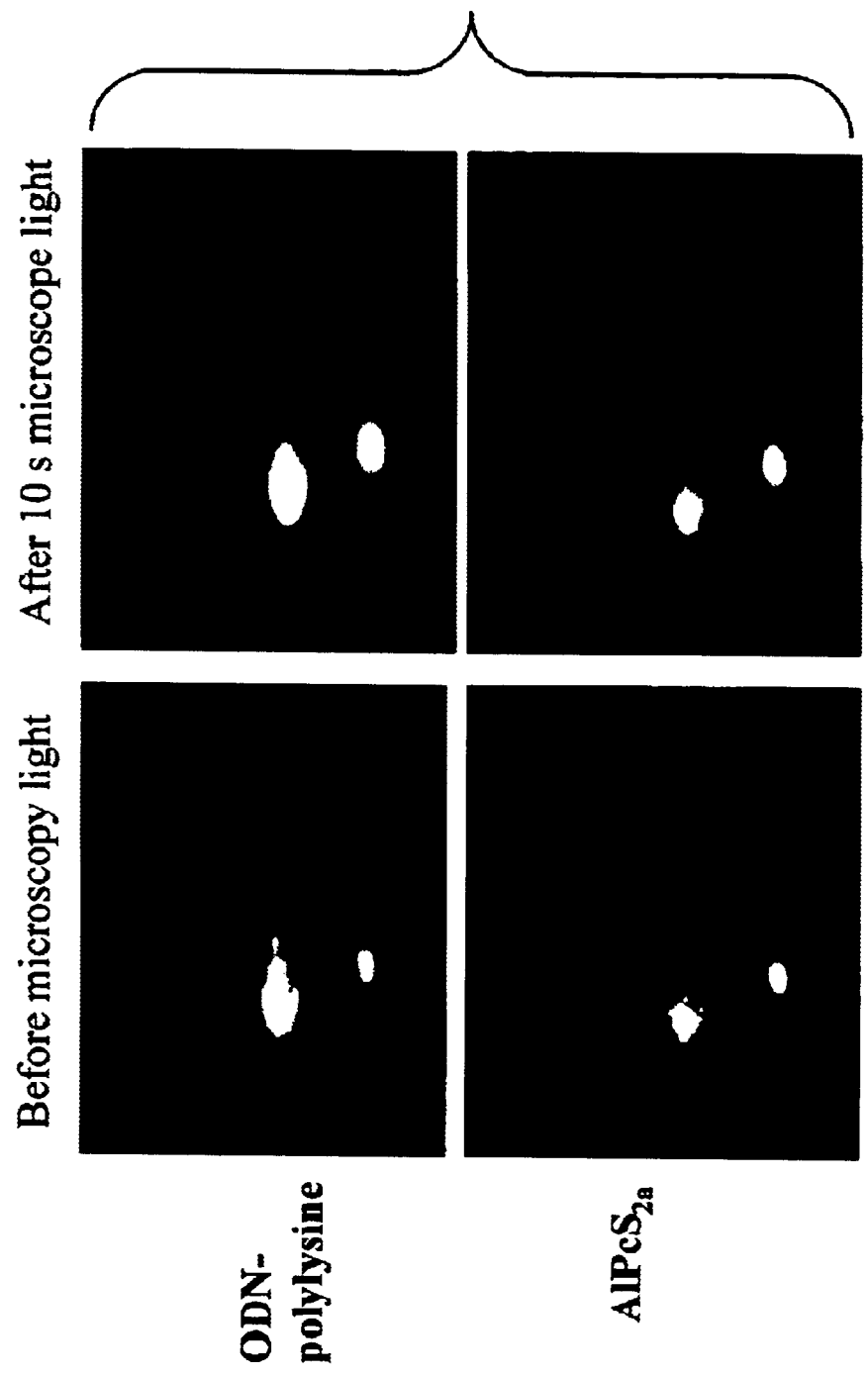
FIG. 17 illustrates relocalization of a fluorescein-labeled oligodeoxynucleotide complex after in vivo injection of $AlPcS_{2a}$ and oligodeoxynucleotide-polylysine complex. Mice were injected with $AlPcS_{2a}$ and oligodeoxynucleotide-polylysine, and a single cell suspension was prepared as described in the text of Example 16. The subcellular localization of $AlPcS_{2a}$ and oligodeoxynucleotide before and after microscope light exposure was studied by fluorescence microscopy as described in Example 16.

FIG. 17 shows that after in vivo administration both AlPcS$_{2a}$ and the fluorescein-labeled ODN are mainly localized to intracellular granula. After light exposure it can be seen that the fluorescence in the granula decreases while the fluorescence in the cytosol increases, indicating relocalization of both AlPcS$_{2a}$ and the ODN from the granules into the cytosol.

Conclusions From Example 16

Example 16 shows that a fluorescein-labeled oligodeoxynucleotide can be relocalized from intracellular granules to the cytosol also after in vivo administration of both the photosensitizer and the oligonucleotide. This indicates that both photosensitizer and oligonucleotide-polylysine complexes are take into tumor cells in vivo in such a way that PCI can be employed, and implies that PCI can be used for a site specific "activation" of therapeutic oligonucleotides in vivo.

Examples 17–27

In the following examples a plasmid containing a gene encoding green fluorescent protein (GFP) has been used as a model to illustrate various aspects of the employment of PCI in delivery and expression of a coding sequence. In these examples the expression of GFP can be viewed as analogous to the expression of a gene or coding sequence, for example a gene or coding sequence encoding a protein, such as a therapeutic protein.

Example 17—PCI Induction of Transfection with a Plasmid-Polylysine Complex

Materials and Methods

A plasmid-polylysine complex was formed by gentle mixing of plasmid DNA (pEGFP-N1, Clontech) and polylysine solutions. 5 µl of DNA (stock solution 1 µg/µl) was diluted with 70 µl 20 mM HBS, and 3.78 µl polylysine (1 µg/µl) was diluted with 71.22 µl 20 mM HBS. After mixing (obtained charge ratio 1.2) the solution was incubated at room temperature for 30 min, then diluted with culture medium to a final volume of 1 ml and added to the cells (1 ml per well).

Transfection. THX-cells were seeded out into 6 well plates (Nunc) (60,000 cells per well). After overnight incubation 20 µg/ml AlPcS$_{2a}$ was added and the cells were incubated for 18 h at 37° C. The cells were washed 3 times with culture medium, incubated for 3 h in sensitizer-free culture medium, transfected with pEGFP/polylysine complex for 2 h in serum-containing medium, and washed in medium for 2 h.

Transfected cells were then washed once with medium and after addition of 2 ml of culture medium the cells were exposed to red light (Phillips TL 20 W/09, filtered through a Cinemoid 35 filter) for 3 or 5 min (control cells were not exposed to the light) and incubated further at 37° C. After 2 days the cells were seeded out into bigger Falcon 3004 dishes and incubated for additional 5 days.

Flow cytometry analysis. The cells were trypsinated, centrifugated, suspend in 400 µl of cultivation medium and filtrated through a 50 µm mesh nylon filter. The cells were analysed in a Facstar plus flow cytometer (Becton Dickinson). Green Fluorecent Protein (GFP) was measured through a 510–530 nm filter after exitation with an argon laser (200 mw) tuned on 488 nm. AlPcS$_{2a}$ was measured through a 650 nm longpass filter after exitation with a krypton laser (50 mw) tuned on 351–356 nm (UV). The data were analysed with Lysis II software (Becton Dickinson). The cells were then prepared for flow cytometry by trypsinizing in 50 µl trypsin and diluted in 450 µl PBS and filtered through a 50 µm mesh nylon filter.

The cells were analyzed in a Facstar plus flow cytometer (Becton Dickinson). FSC-H and FSC-W were measured to discriminate dublett cells and SSC-H to detect cellular granularity. The cytometer was calibrated for green fluorescence by measuring fluorescent beads with known intensity.

Green Fluorescent Protein (GFP) was measured through a 510–530 nm filter after excitation with an argon laser (200 mw) tuned on 488 nm. AlPcS2a was measured through a 650 nm longpass filter after excitation with a krypton laser (50 mw) tuned on 351–356 nm. The data were analyzed with Lysis II software (Becton Dickinson).

Results

Figure 18:
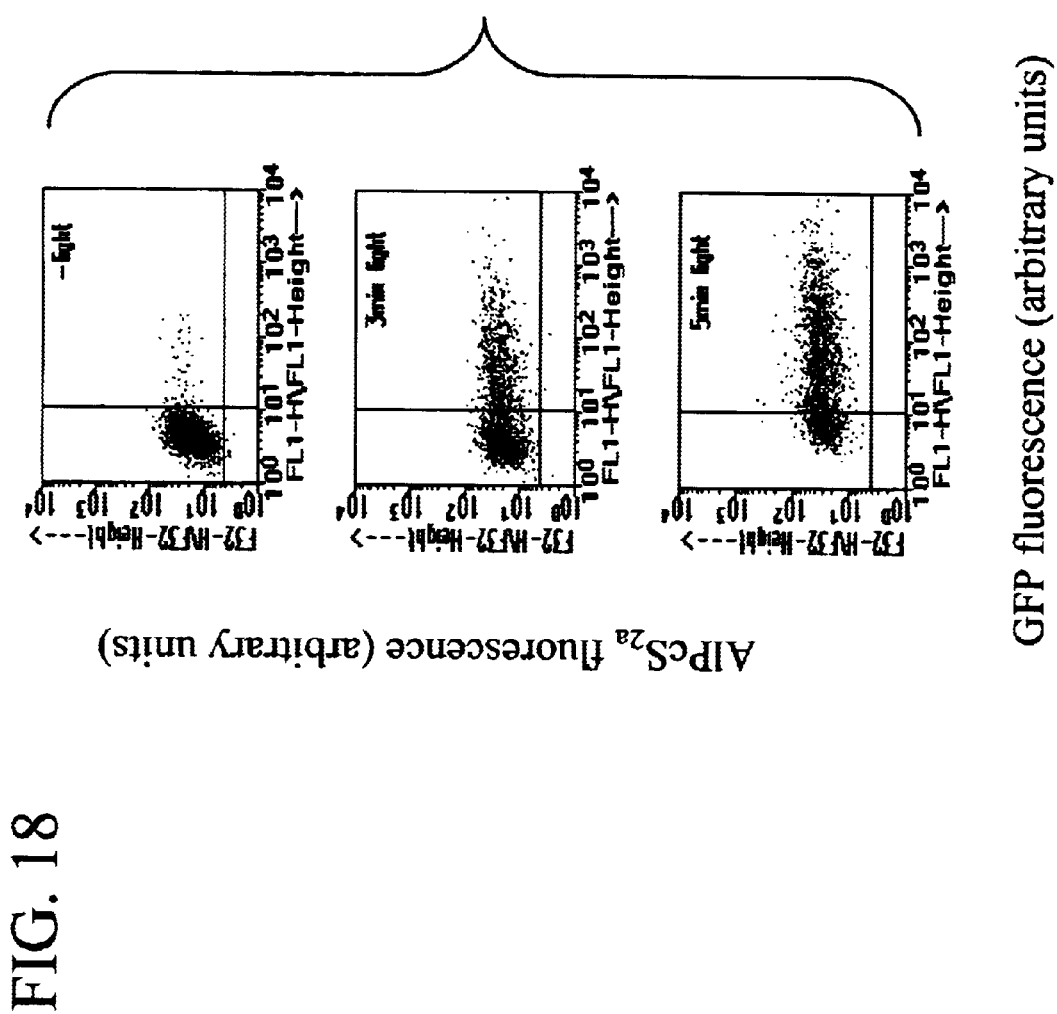
FIG. 18 illustrates PCI induced transfection with a plasmid-polylysine complex. Cells were incubated with $AlPcS_{2a}$ and transfected as described in the text of Example 17. The expression of green fluorescent protein (GFP) in the transfected cells was analysed by flow cytometry as described. The cells in the upper right quadrant were regarded as positive for GFP-expression. Light exposure times are indicated on the Figure.

From FIG. 18 it can clearly be seen that the amount of GFP-expressing cells increased strongly as a result of the light treatment. In this experiment there was an increase from about 1% positives at no light treatment to about 48% after 5 min light exposure, indicating that the light treatment of PCI gives strong and very specific increase in the efficiency of transfection.

Example 18—PCI Induction of Transfection with a Plasmid-Polylysine Complex.

Materials and Methods

A plasmid-polylysine complex was formed by gentle mixing of plasmid DNA (pEGFP-N1, Clontech) and polylysine solutions. 5 µl of DNA (stock solution 1 µg/µl) was diluted with 70 µl 20 mM HBS, and 3.78 µl polylysine (1 µg/µl) was diluted with 71.22 µl 20 mM HBS. After mixing (obtained charge ratio 1.2) the solution was incubated at room temperature for 30 min, then diluted with culture medium to a final volume of 1 ml and added to the cells (1 ml per well).

Transfection. THX-cells were seeded out into 6 well plates (Nunc) (60 000 cells per well). After overnight incubation 20 µg/ml AlPcS$_{2a}$ was added and the cells were incubated for 18 h at 37° C. The cells were washed 3 times with culture medium, incubated for 1 h in sensitizer-free culture medium and then transfected with pEGFP/polylysine complex for 2 h in serum-containing medium.

Transfected cells were washed once with the medium and after addition of 2 ml of culture medium exposed to red light (Phillips TL 20 W/09, filtered through a Cinemoid 35 filter) for 3 or 5 min (control cells were not exposed to the light) and incubated further at 37° C. After 2 days the cells were seeded out into bigger Falcon 3004 dishes and incubated for additional 5 days. The cells were then analysed by flow cytometry as described in Example 17.

Results

Figure 19:
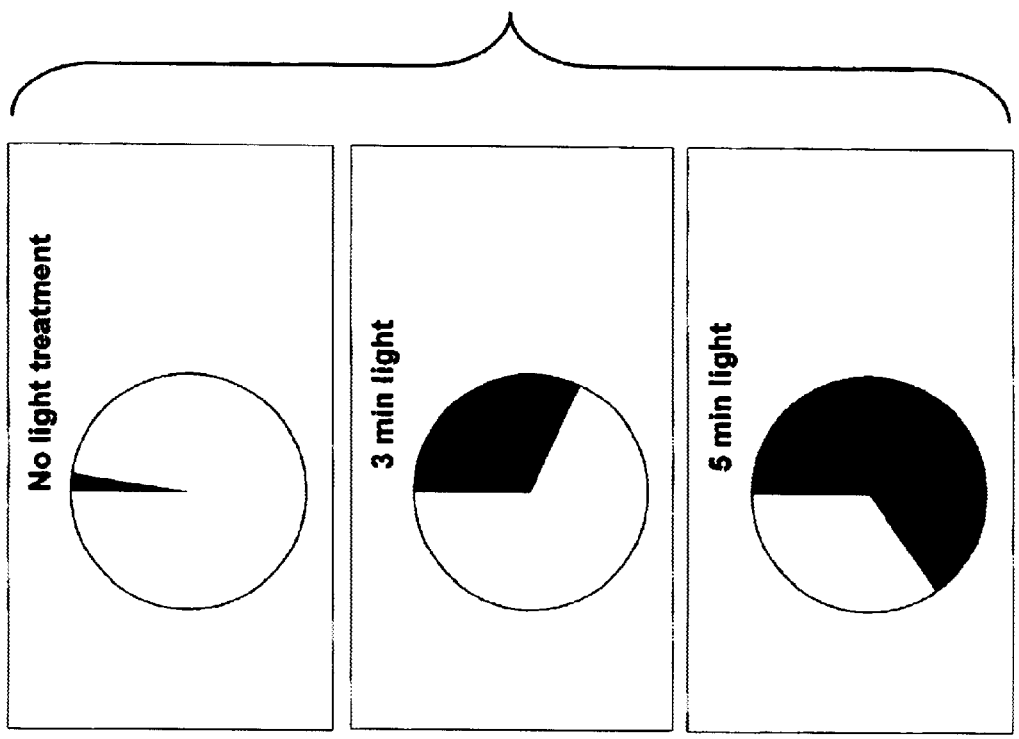
FIG. 19 illustrates PCI-induced transfection by a complex of plasmid DNA and polylysine. The experiment was performed as described in the text of Example 18. The white circle represents the total population of living cells, the black sector represents the fraction of cells that was positive for GFP-expression as determined by flow cytometry analysis. Light exposure times are indicated on the Figure.

As can be seen from FIG. 19, the light treatment lead to a strong increase in the percentage of the cells that expressed GFP. Thus, the fraction of the cells that were positive for this reporter molecule increased from 2.5% at no light treatment to 65% after 5 min light exposure. Consequently, in a light directed manner PCI can substantially increase the efficiency of delivery of a functional gene to cells.

Conclusions From Examples 17 and 18

In Examples 17 and 18 it is shown that in vitro PCI can greatly increase the number of cells expressing GFP after delivery of the DNA as a polylysine complex. Thus, e.g. in Example 18 the fraction of the cells that were positive for the GFP reporter molecule increased from 2.5% at no light treatment to 65% after 5 min light exposure.

Example 19—Transfection of AlPcS$_{2a}$-Treated THX-Cells With pEGFP-N1 Complexes With Polylysine Made up in HEPES or in Water Materials and Methods pEGFP-N1-polylysine complexes (DNA concentration ~5 µg/ml, charge ratio 1.7) were formed by gentle mixing of DNA and polylysine solutions. 5 μl of DNA (stock solution 1 μg/μl) was diluted with 70 μl water or the same volume of 20 mM HBS, and 5.33 μl polylysine (1 μg/μl) was diluted with 69.67 μl water or the same volume of 20 mM HBS. DNA solution in water was mixed with polylysine in water and DNA in HBS was mixed with polylysine in HBS. The obtained mixtures were incubated at room temperature for 30 min, then diluted with culture medium to a final volume of 1 ml and added to the cells (1 ml per well).

THX-cells were seeded out into 6 well Nunc plates (60 000 cells per well). After overnight incubation 20 μg/ml AlPcS$_{2a}$ was added and the cells were incubated for 18 h at 37° C. The cells were then washed 3 times with medium without serum and transfected with the pEGFP-N1 polylysine complex prepared in water or HBS for 6 h. Transfected cells were washed once with culture medium and after addition of 2 ml of culture medium the cells were exposed to red light (Phillips TL 20 W/09, filtered through a Cinemoid 35 filter) for 4 min (control cells were not exposed to the light) and incubated further at 37° C. for 80 h before analysis by flow cytometry as described above (see Example 17).

Results

Figure 20:
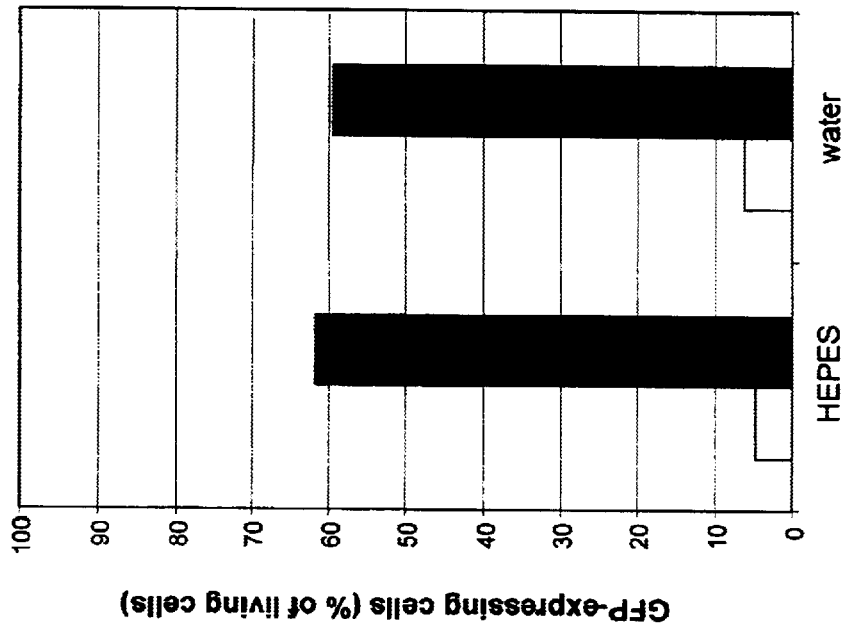
FIG. 20 illustrates transfection of $AlPcS_{2a}$-treated THX-cells with pEGFP-N 1 complexes with polylysine made up in HEPES or in water. The experiment was performed as described in the text of Example 19. The white bars represent no light exposure, the black bars represent 4 min light exposure.

From FIG. 20 it can be seen that a DNA-polylysine complex made in water was as efficient as an analogous complex made in HEPES-buffer. Thus, in both cases the light treatment increased the percentage of positive cells by about 10 times.

Conclusions From Example 19

In Example 19 it is shown that PCI works also if the DNA-complex is made up in water. This is important since it has been reported (Dr. Ernst Wagner, oral presentation at 6$^{th}$ Symposium on Gene Therapy, Berlin, May 1998) that DNA-polycation complexes made up in water may have advantages for use in vivo as compared to complexes made up in buffer.

Example 20—Transfection Efficiency after PCI with Different Doses of AlPcS2a

Materials and Methods

THX-cells were seeded out into 6 well plates (60 000 cells per well). After overnight incubation AlPcS$_{2a}$ in concentrations of 5 μg/ml or 40 μg/ml was added, and the cells were incubated for 18 h at 37° C. The cells were then washed 3 times with culture medium and transfected with pEGFP-N1-polylysine complex (amount of plasmid 5 μg/ml, charge ratio 1.2, see Example 17) for 6 h. The transfected cells were washed once with medium, and after addition of 2 ml of culture medium the cells were exposed to red light (Phillips TL 20 W/09, filtered through a Cinemoid 35 filter) for 2 or 4 min (control cells were not exposed to the light) and incubated further at 37° C. for 40 hrs before flow cytometry analysis (see Example 17).

Results

Figure 21:
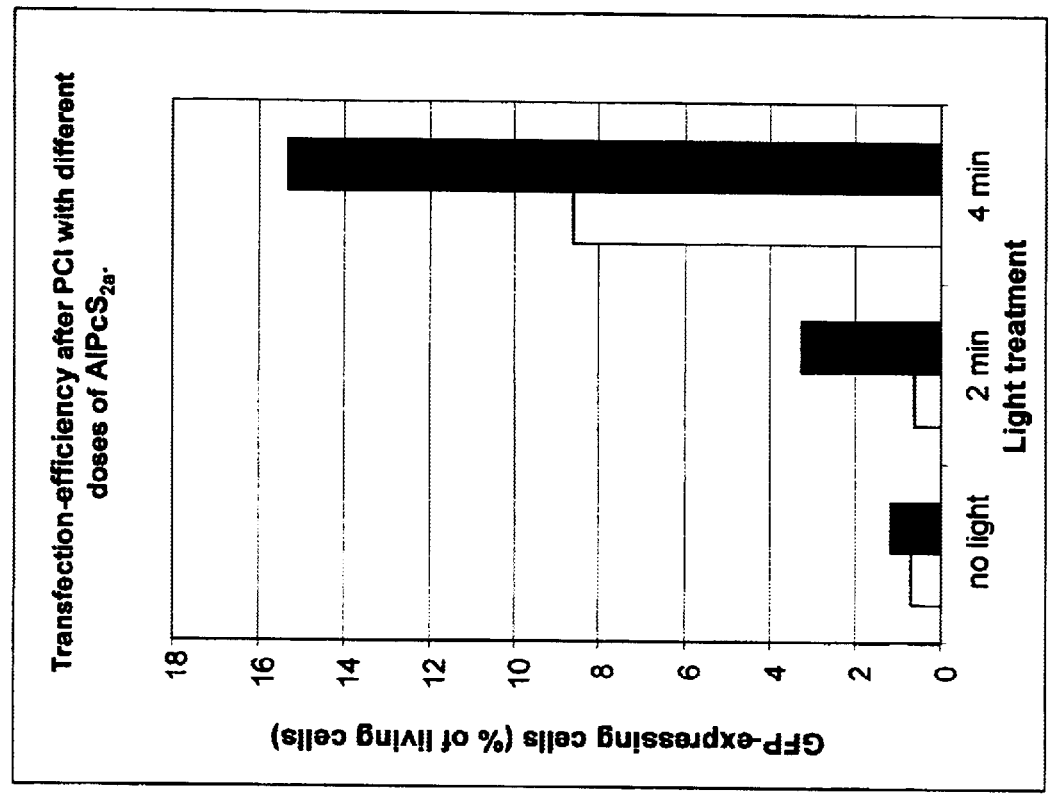
FIG. 21 illustrates transfection efficiency after PCI with different doses of AlPcS$_{2a}$. Cells were treated with different doses of the photosensitizer, transfected with a plasmid DNA-polylysine complex and analysed by flow cytometry as described in the text of Example 20. the white bars represent an AlPcS$_{2a}$ dose of 5 µg/ml, while the black bars represent 40 µg/ml.

It can be seen (FIG. 21) that the percentage of transfected cells increased with increasing photosensitizer concentration. Since photosensitizer often accumulate preferentially in tumors as compared to surrounding tissues, this means that in many cases the effect of the light treatment in PCI will be greater on tumor cells than on surrounding tissue adding further to the specificity obtainable in PCI-induced gene therapy.

Conclusions From Example 20

In Example 20 it can be seen (FIG. 21) that the effect of PCI increased with increasing photosensitizer concentration. Since photosensitizer often accumulate preferentially in tumors as compared to surrounding tissues, this means that in many cases the effect of the light treatment in PCI will be greater on tumor cells than on surrounding tissue possibly adding further to the specificity obtainable in PCI-induced gene therapy of tumors.

Example 21—Transfection of AlPcS$_{2a}$-Treated BHK-21-Cells With a Polylysine Complex of pEGFP-N1

Materials and Methods

The pEGFP-N1 polylysine complex was formed by gentle mixing of DNA and polylysine solutions. To get the charge ratio 1.2, 5 μl of DNA (stock solution 1 μg/μl) was diluted with 70 μl 20 mM HBS, and 3.78 μl polylysine (1 μg/μl) was diluted with 71.22 μl 20 mM HBS. After mixing the DNA solution with the polylysine solution, the obtained mixture was incubated at room temperature for 30 min, then diluted with culture medium to a final volume of 1 ml and added to the cells (1 ml per well).

Baby Hamster Kidney cells (BHK-21) were seeded out into 6 well plate (60 000 cells per well). After overnight incubation 20 μg/ml AlPcS$_{2a}$ was added and the cells were incubated for 18 h at 37° C. The cells were then washed 3 times with culture medium and transfected with pEGFP-N1-polylysine complex (amount of plasmid 5 μg/ml, charge ratio 1.2) for 6 h. The transfected cells were washed once with the medium and after addition of 2 ml of culture medium the cells were exposed to red light (Phillips TL 20 W/09, filtered through a Cinemoid 35 filter) for 7 or 9 min (control cells were not exposed to the light) and incubated further at 37° C. for 44 h before flow cytometry analysis (see Example 17).

Results

Figure 22:
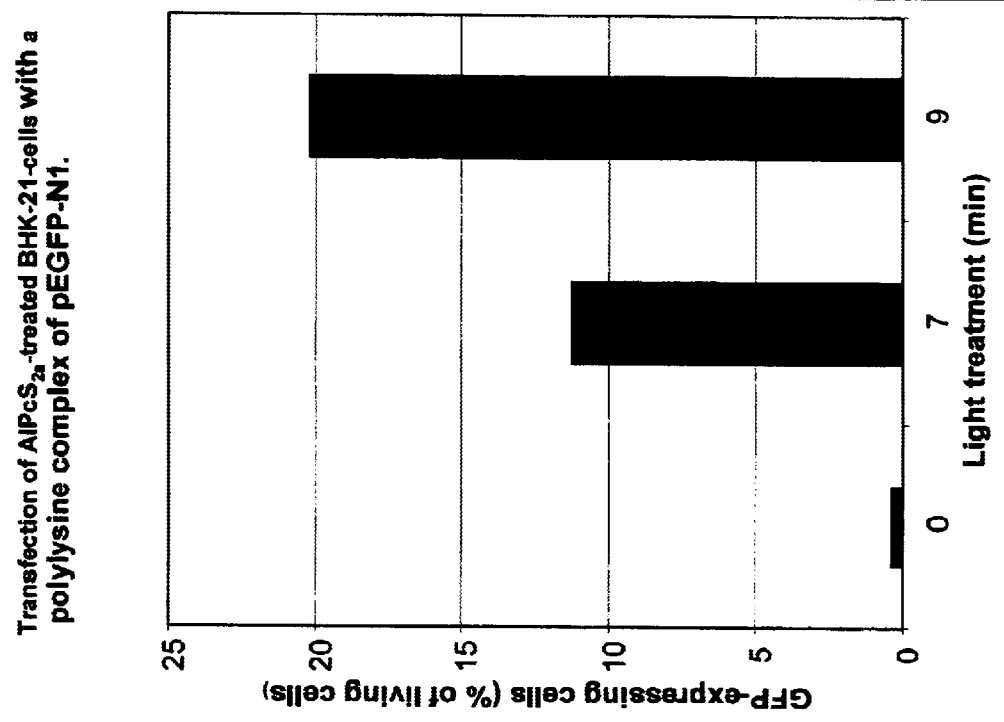
FIG. 22 illustrates transfection of AlPcS$_{2a}$-treated BHK-21-cells with a polylysine complex of pEGFP-N1. Cells were treated with photosensitizer and transfected with a complex of plasmid DNA and polylysine as described in the text of Example 21. After light treatment the cells were analysed by flow cytometry.

From FIG. 22 it is obvious that PCI-induced transfection works very well also on BHK-21 baby hamster kidney cells, with a 55 times difference in the percentage of positive cells between no and 9 min light exposure.

Example 22—Transfection of AlPcS$_{2a}$-Treated HCT-116 Cells With a Polylysine Complex of pEGFP-N1

Materials and Methods

HCT 116 human colon cancer cells were subcultured in 5 wells in a 24 well tissue culture plate with 50.000 cells/well. Culture medium used under the entire procedure was RPMI containing 2 mM glutamine, 100 U/ml penicillin and 100 μg/ml streptomycin (all Bio-Whittaker) and 10% FCS (Integro b.v., Holland). Cells were cultured in an incubator containing 5% $CO_2$.

After 6–7 h of culturing, the cells were added 20 μg/ml AlPcS $2_a$ and incubated over night at 37° C. The cells were then washed twice in culture medium and added a DNA-polylysine complex. This complex was made after following procedure:

To 10 μl of 1 μg/μl DNA (pEGFP-N1, Clontech) was added 140 μl sterile water.

To 13.8 μl of 1 μg/μl poly-1-lysin (MW 20,700, Sigma) was added 136.2 μl sterile water.

The DNA and poly-1-lysin solutions were mixed together by gently pipetting up and down, and incubated at room temperature for 30 min.

The DNA-polylysine complex was diluted to a total volume of 2 ml in culture medium and added to the cells, 250 μl in each well. The cells were incubated with the mixture for 4 h and then washed 2 times in culture medium. The cells were then exposed to red light (Phillips TL 20

W/09, filtered through a Cinemoid 35 filter) for respectively 0, 4, 6, 8 and 9 minutes and incubated further at 37° C. for 48 h. The cells were then analyzed by flow cytometry as described in Example 17.

Figure 23:
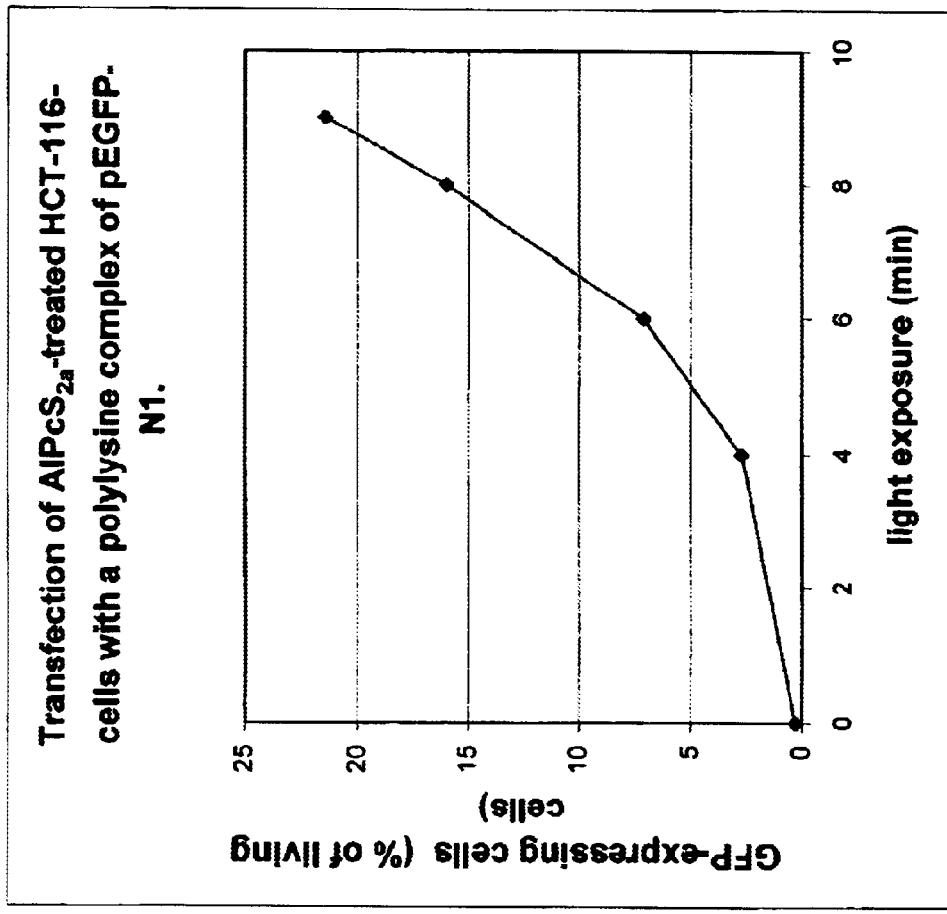
FIG. 23 illustrates transfection of AlPcS$_{2a}$-treated HCT-116-cells with a polylysine complex of pEGFP-N1. HCT-116 cells were treated with photosensitizer and transfected with a complex of plasmid DNA and polylysine as described in the text of Example 22. After light treatment the cells were analysed by flow cytometry.

As can be seen from FIG. 23, the light treatment induced a very substantial increase in the amount of cells expressing the reporter molecule GFP. As compared to the value at no light exposure, 9 min light treatment lead to an increase of about 65 times in the percentage of cells that expressed GFP.

Conclusions From Examples 21 and 22

Examples 21 and 22 show that PCI-induced transfection works also on baby hamster kidney (BHK-21) cells (Example 21) and human colon cancer (HCT116) cell lines (Example 22), in addition to what has already been shown for a human melonoma cell line. This indicates that PCI-induced gene therapy could be applicable on a lot of different cells and tissues, making it possible to use the method for gene therapy of a variety of diseases.

Example 23—PCI-Induced Transfection of $TPPS_{2a}$-Treated THX-Cells With pEGFP-N1-Polylysine Complex Materials and Methods A pEGFP-N1-polylysine complex (5 µg DNA, charge ratio 1.2 was prepared as described above (see Example 17).

THX-cells were seeded out into 6 well plates (60 000 cells per well). After overnight incubation 2 µg/ml of the photosensitizer $TPPS_{2a}$ was added and the cells were incubated further for 18 h at 37° C. The cells were then washed 3 times with culture medium and transfected with the pEGFP-N1-polylysine complex for 6 h. The transfected cells were washed once with medium, and after addition of 2 ml of culture medium the cells were exposed to blue light (Appl. Photophysics, Nood. 3026, London) for 30, 60, 90, 120 or 150 s (control cells were not exposed to the light) and incubated further at 37° C. After 2 days the cells were seeded out into bigger 3004 dishes and incubated further so that the total incubation time before flow cytometry analysis was 108 h.

Results

Figure 24:
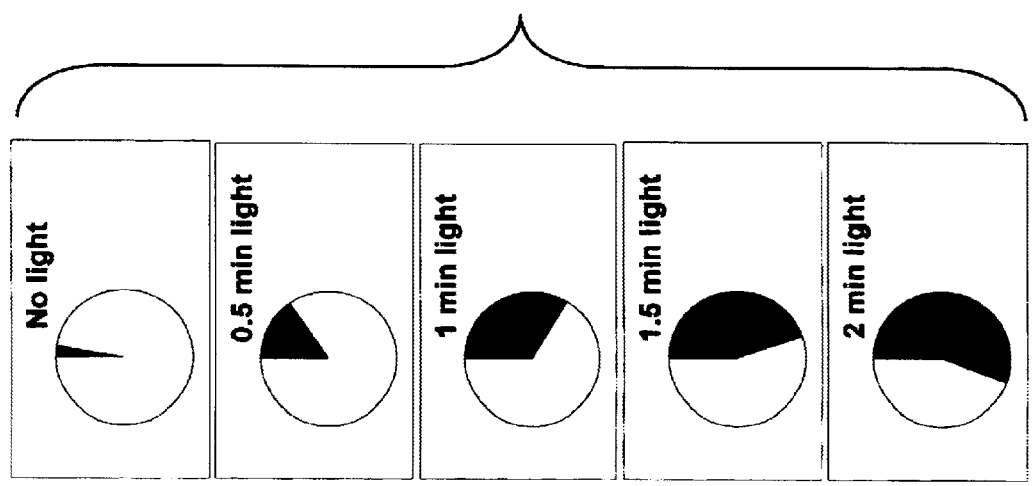
FIG. 24 illustrates PCI induced transfection of TPPS$_{2a}$-treated THX-cells. Cells were treated with TPPS$_{2a}$ and transfected with a complex of plasmid DNA and polylysine as described in the text of Example 23. After light treatment the cells were analysed by flow cytometry. The white circle represents the total population of living cells, the black sector represents the fraction of cells that was positive for GFP-expression. Light exposure times are indicated on the Figure.

As can be seen from FIG. 24, a substantial transfection-enhancing effect of the PCI light treatment can be observed also using $TPPS2_a$ as the photosensitizer.

Conclusions From Example 23

Example 23 shows that also other photosensitizers than $AlPcS_{2a}$ can be used for PCI-induced gene therapy. Thus, the effect with the sensitizer $TPPS_{2a}$ is essentially the same as for $AlPcS_{2a}$.

Example 24—Transfection of $AlPcS_{2a}$-Treated THX Cells With a Polyarginine Complex of pEGFP-N1

Materials and Methods

A pEGFP-N1-polyarginine complex (DNA concentration ~5 µg/ml, charge ratio 1.2) was made from poly-arginine MW 42400 (Sigma) preparation in the same way as described above (see Example 17) for polylysine-complexes.

THX-cells were seeded out into 6 well plates (60 000 cells per well). After overnight incubation 20 µg/ml $AlPcS_{2a}$ was added and the cells were incubated for 18 h at 37° C. The cells were then washed 3 times with culture medium and transfected with the pEGFP/polyarginine complex for 6 h. Transfected cells were washed once with medium and after addition of 2 ml of culture medium the cells were exposed to red light (Phillips TL 20 W/09, filtered through a Cinemoid 35 filter) for 2 or 4 min (control cells were not exposed to the light) and incubated further at 37° C. for 40 hrs before flow cytometry analysis.

Results

Figure 25:
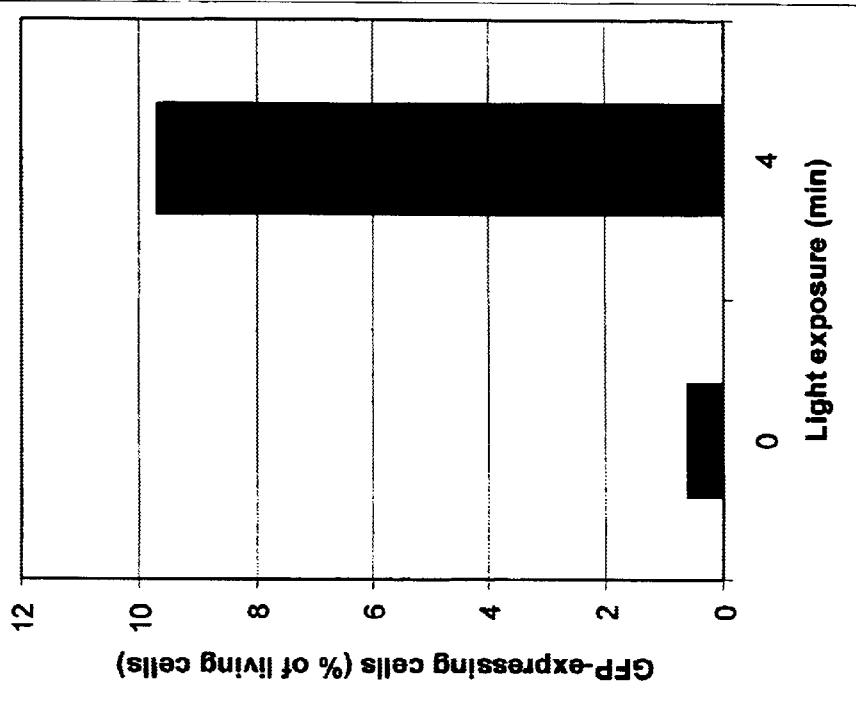
FIG. 25 illustrates transfection of AlPcS$_{2a}$-treated THX-cells with a polyarginine complex of pEGFP-N1. THX-cells were incubated with AlPcS$_{2a}$ transfected with plasmid-polyarginine complex, subject to light treatment and analysed as described in the test of Example 24.

FIG. 25 shows that PCI can also induce transfection when the plasmid DNA is delivered as a complex with the polycation poly-arginine.

Example 25—PCI-Induced Transfection of $AlPcS_{2a}$-Treated THX-Cells With Polyethyleneimine Complexes of pEGFP-N1

Materials and Methods

Polyethyleneimine (PEI) (50 kDa, Sigma) was used as a 10 mM aqueous stock solution (9 mg of the 50% (w/v) commercial solution diluted in 10 ml of water). The solution was neutralized with HCl and filtered (Millipore, 0.2 mm). 5 µl pEGFP-N1 DNA (stock solution 1 µg/µl) and 2.55 µl (to get the charge ratio 1.7) or 3 µl (to get the charge ratio 2.0) PEI stock solution were each diluted in water to 50 µl and vortexed. After 10 min the DNA and PEI solutions were mixed and the resulting solutions were vortexed. After 10 more minutes the solution was diluted with culture medium to 1 ml and added to the cells.

THX-cells were seeded out into 6 well plates (60 000 cells per well). After overnight incubation 20 µg/ml $AlPcS_{2a}$ was added and the cells were incubated for 18 h at 37° C. The cells were then washed 3 times with culture medium and transfected with the DNA/PEI complexes for 6 h. The transfected cells were washed once with medium and after addition of 2 ml culture medium the cells were exposed to red light (Phillips TL 20 W/09, filtered through a Cinemoid 35 filter) for 4 min (control cells were not exposed to the light) and incubated further at 37° C. for 40 h. GFP expression was analysed by flow cytometry as described in Example 17.

Results

Figure 26:
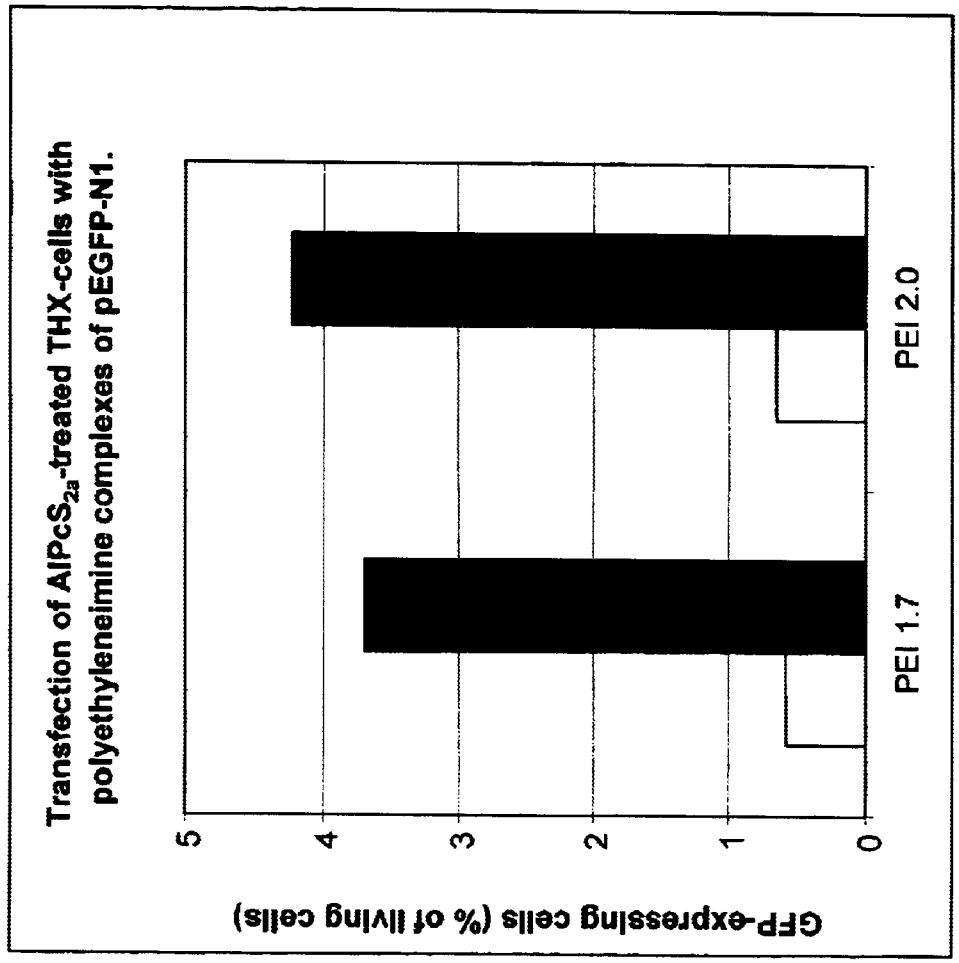
FIG. 26 illustrates transfection of AlPcS$_{2a}$-treated THX-cells with polyethyleneimine complexes of pEGFP-N1. Cells were transfected with a plasmid-polyethyleneimine complex, subject to light treatment and analysed as described in the text of Example 25. The white bars represent no light exposure, the black bars 4 min exposure. The charge ratios of the complexes are indicated on the Figure.

As shown in FIG. 26, PCI can induce gene-expression also when a plasmid is delivered to the cells as a complex with polyetyleneimine.

Conclusions From Examples 24 and 25

Examples 24 and 25 show that also other polycations than polylysine can be used for complexing DNA for use in PCI-induced transfection. Thus, PCI works both with polyarginine (Example 24) and with polyethyleneimine (Example 25), an agent that has advantageous properties for in vivo use.

Example 26—Two-Dimensional Resolution of Transfection after PCI

Materials and Methods

A pEGFP-N1-polylysine complex was formed by gentle mixing of DNA and polylysine solutions. 5 µl of DNA (stock solution 1 µg/µl) was diluted with 70 µl water and 5.33 µl polylysine (1 µg/µl) with 69.67 µl water (final charge ratio 1.7) After 30 min incubation at room temperature the solution was diluted with culture medium to a final volume 1.7 ml and 1 ml was added to the cells.

Figure 27:
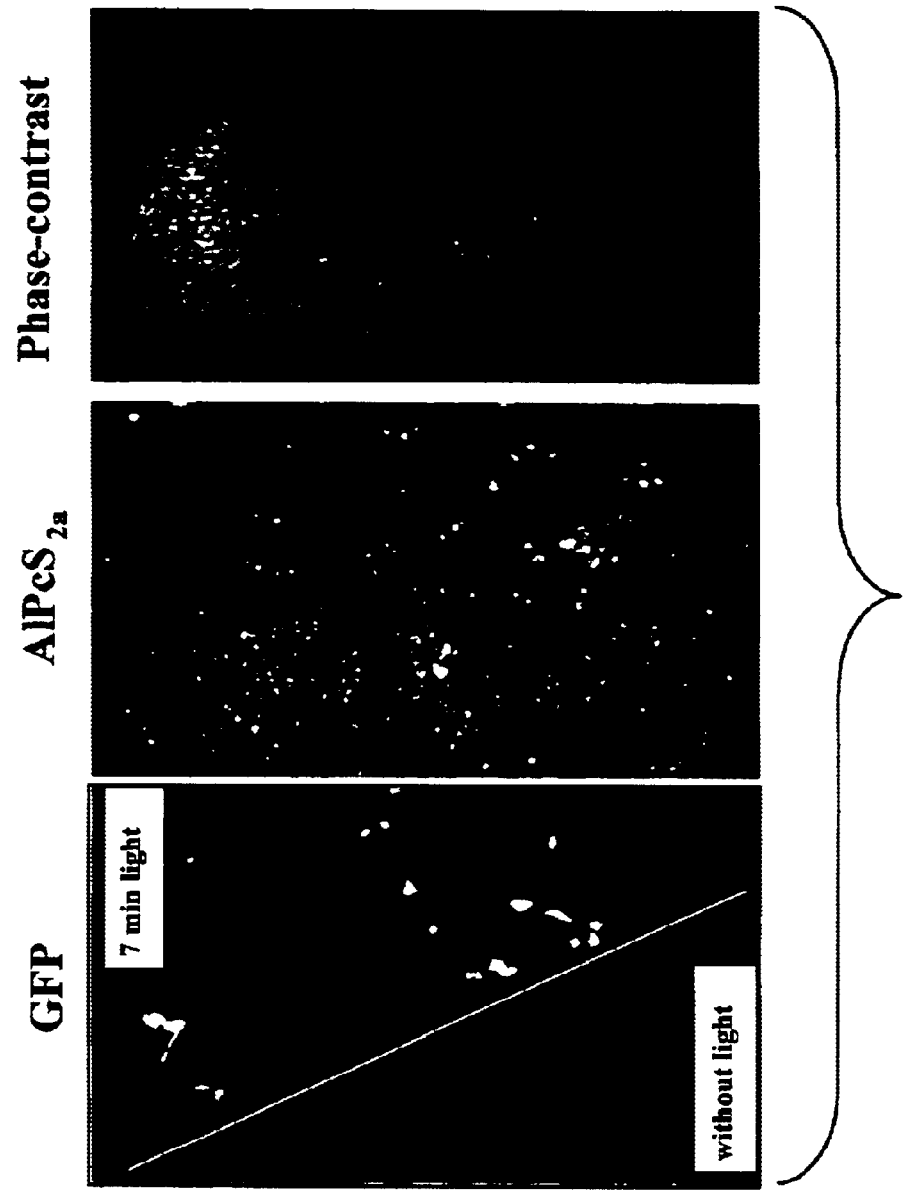
FIG. 27 illustrates two dimensional resolution of transfection after PCI as described in detail in Example 26. Expression of GFP in HCT-116 cells after 6 h transfection with pEGFP-N1 polylysine complex (3 µg/ml DNA, C.R. 1.7). Cells were incubated 18 h with 20 µg/ml AlPcS$_{2a}$ before the transfection and 40 h after transfection before analysis by microscopy. Half of the dish after transfection was irradiated with red light for 7 min and half of the dish was protected from light (indicated on the Figure). The border between the irradiated and the non-irradiated area is indicated by a while line on the GFP panel. The conditions for microscopy were 10×1.25 magnification, 5 s light exposure for GFP fluorescence, 1 s for AlPcS$_{2a}$ and 50 ms for phase contrast.

200 000 HCT116 cells (human colon carcinoma) were seeded out into a Falcon 3001 dish. After overnight incubation 20 µg/ml $AlPcS_{2a}$ was added and the cells were incubated for 18 h at 37° C. The cells were then washed 3 times with culture medium and transfected with the pEGFP-N1-polylysine for 6 h. After transfection half of the dish was exposed to red light (Phillips TL 20 W/09, filtered through a Cinemoid 35 filter) for 7 min while the rest of the dish was protected from light. 40 h later the expression of EGFP in both halves of the dish was studied by fluorescence and phase contrast microscopy (objective with 10 times magnification, the microscope was equipped with 450–490 band pass excitation filter) essentially as described in Example 13.
Results FIG. 27 shows that location specific expression of GFP is obtained upon transfection and exposure to light. Expression occurs in areas exposed to light but not in areas kept dark. The location of photosensitizer and cells are not affected by exposure to light. This result shows that cells and photosensitizer are located in all areas of the slide, but the gene delivered by the method of the invention is localized and expressed only in cells exposed to light.

Conclusions From Example 26

Example 26 shows the precision in the induction of transfection obtainable by the light treatment. It can easily be seen that almost no cells were positive for GFP-expression in an area that was shielded against light, while a lot of positive cells were distributed all over an illuminated area. This clearly illustrates the potential of using PCI to obtain location specific expression of a therapeutic gene in vivo.

Example 27—PCI-Induced GFP-Expression After In Vivo Injection of AlPcS$_{2a}$ and pEGFP-N1 Polylysine Complex and Ex Vivo Light Treatment Materials and Methods A complex containing 50 mg pEGFP-N1 and 53 mg polylysine (charge ratio 1.7) was made as follows. 5.3 ml polylysine (10 mg/ml) was diluted with 10 ml Hepes buffer (20 mM pH 7.4) and mixed with 10 ml pEGFP-N 1 (stock solution 5 mg/ml). The mixture was incubated at room temperature for 30 min before the injection.

40 mg/kg AlPcS$_{2a}$ was injected i.p. into tumor bearing mice (the animal model is described in Example 16). The mice were kept in a cage covered by aluminum paper for 48 h prior to DNA-injection. The pEGFP-N1/polylysine complex (total volume 25 ml) was injected directly into the tumor. 6 h after the injection, the tumor was removed and a single cell suspension was prepared by enzymatic digestion (see Example 16). Isolated cells were seeded out into Nunc 6 wells plate (200 000 cells per well) and exposed to red light (Phillips TL 20 W/09, filtered through a Cinemoid 35 filter) for 2, 5, 7 or 10 min (control cells were not exposed to light). 140 h later the expression of GFP was analyzed by flow cytometry as described in Example 17.

Results

Figure 28:
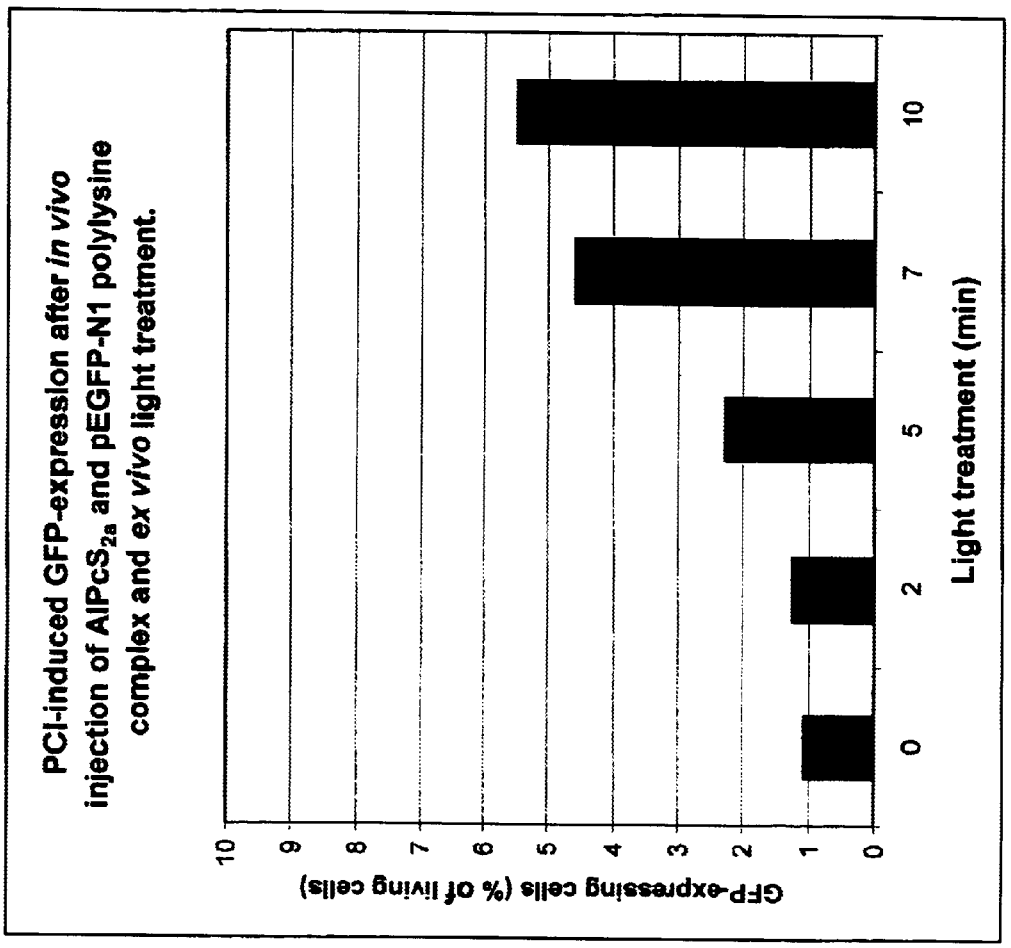
FIG. 28 illustrates PCI-induced GFP-expression after in vivo injection of AlPcS$_{2a}$ and pEGFP-N1 polylysine complex and ex vivo light treatment. A pEGFP-N1-polylisine complex was injected intratumorally in AlPcS$_{2a}$-treated mice as described in the text to Example 27. 6 h after the injection the tumor was removed, and the tumor cells were prepared, subjected to light treatment and analysed as described.

Flow cytometry showed a 5×increase in GFP-expressing cells after light treatment and a clear light dose-response (FIG. 28). This indicates that both photosensitizer and plasmid-polylysine complexes are take into tumor cells in vivo in such a way that PCI can be employed and that PCI works when the light treatment is given ex vivo.

Conclusions From Claim 27

In Example 27 both the photosensitizer and a plasmid polylysine complex were administered in vivo. The results showed a 5 times increase in GFP-expressing cells after light treatment ex vivo and a clear light dose-response (FIG. 15). This indicates that both photosensitizer and plasmid-polylysine complexes are take into tumor cells in vivo in such a way that light treatment can lead to a light-dependent and site-specific "activation" of therapeutic genes in vivo.

Conclusions From Examples 13–27

When the data in the above experiments are taken together in effect it means that the PCI light treatment can be used to turn on the expression of a therapeutic gene at a specific location in the body, e.g. in a tumor. For many kinds of putative therapeutic genes such site specific expression can be very advantageous, since expression of a therapeutic gene outside the diseased area often can give very severe side effects. Examples of therapeutic genes that could with benefit be used with PCI are: (i) genes coding for "suicide enzymes" (e.g. Herpes Simplex Virus thymidine kinase, cytidine deaminase, D-amino acid oxidase and so on); (ii) genes encoding toxins or parts of toxins (e.g. diphtheria toxin, diphtheria toxin A-chain, ricin, gelonin); (iii) genes encoding recombinant immunotoxins; (iv) genes encoding cytokines (e.g. tumor necrosis factor-α, transforming growth factor-β, interleukin-12 and other interleukins, colony-stimulating factors, chemokines and others); genes encoding immunostimulatory molecules (e.g. HLA-B7, B7.1 costimulatory protein and others). Other examples of putative therapeutic genes that could be used with PCI are genes encoding: ribozymes, RNA antisense oligonucleotides, aptamers, triplex forming RNA, intracellular recombinant antibodies, antiangiogenetic factors, angiogenetic factors, anti-inflammatory molecules and so on.

What is claimed is:

1. A method for introducing a nucleic acid into a cytosol of a cell, comprising:

a) delivering a photosensitizing compound and the nucleic acid directly to the cell, wherein said photosensitizing compound and said nucleic acid are taken up into an intracellular compartment of the cell;

b) irradiating the cell with light of a suitable wavelength to activate the photosensitizing compound so that the membrane surrounding the intracellular compartment is disrupted, releasing the nucleic acid into the cytosol of the cell without killing the cell.

2. The method of claim 1, wherein the nucleic acid sequence comprises DNA, RNA, or a combination thereof.

3. The method of claim 2, wherein the DNA or RNA comprises a plasmid, a ribozyme, an antisense oligonucleotide, an aptamer, a triplex forming oligonucleotide, a peptide nucleic acid, or a combination thereof.

4. The method according to claim 1, wherein the photosensitizing compound is a porphyrin, a phthalocyanine, a purpurin, a benzoporphyrin, a napthalocyanine, a cationic dye, a tetracycline, or a lysosomotropic weak base or derivative thereof.

5. The method according to claim 1, further comprising facilitating, with a vector molecule, the uptake of the nucleic acid which is to be released into the cytosol, wherein the vector molecule is conjugated to or administered with the nucleic acid to be released into the cytosol.

6. The method according to claim 1, wherein the step of irradiating includes selecting a light dose and wavelength and a photosensitizing compound so that after the irradiation, a portion of the living cells are killed.

7. The method of claim 1, wherein the step of delivering further comprises delivering carrier molecules to the cell wherein at least one carrier molecule is conjugated to or administered with the nucleic acid to be released into the cytosol.

8. The method of claim 1, wherein the nucleic acid to be released into the cytosol is subsequently expressed in the cell or on the cell surface.

9. The method of claim 8, wherein the cell is an antigen-presenting cell.

10. The method of claim 2, wherein the DNA or RNA encodes an angiogenic factor.

11. A method for introducing a molecule to be released into a cytosol of a living cell, comprising:

first delivering a photosensitizing compound to the cell, wherein the photosensitizing compound is taken up into an intracellular compartment of the cell; followed by delivering a molecule to be released into the cytosol directly to the cell, wherein the molecule to released into the cytosol is taken up into an intracellular compartment of the cell.

irradiating the cell with light of a suitable wavelength to activate the photosensitizing compound so that the membrane surrounding the intracellular compartment is disrupted, releasing the molecule into the cytosol of the cell without killing the cell.

12. The method according to claim 5, wherein the vector molecule is a plasmid.

13. The method according to claim 1, wherein the step of delivering further comprises delivering carrier molecules to the cell, wherein at least one carrier molecule is attached to the photosensitizing compound.

14. A method according to claim 13 wherein the carrier molecule is an antibody.

* * * * *